(12) United States Patent
Peterson et al.

(10) Patent No.: US 6,620,176 B1
(45) Date of Patent: Sep. 16, 2003

(54) MEDICAL GRAFT CONNECTOR AND METHODS OF MAKING AND INSTALLING SAME

(75) Inventors: Alex Alden Peterson, Maple Grove, MN (US); Paul J. Hindrichs, Plymouth, MN (US); Mark D. Wahlberg, St. Paul, MN (US); Todd Allen Berg, Plymouth, MN (US); Jon Patrick St. Germain, Elk River, MN (US)

(73) Assignee: St. Jude Medical ATG, Inc., Maple Grove, MN (US)

( * ) Notice: Subject to any disclaimer, the term of this patent is extended or adjusted under 35 U.S.C. 154(b) by 378 days.

(21) Appl. No.: 09/663,955

(22) Filed: Sep. 19, 2000

Related U.S. Application Data

(62) Division of application No. 09/187,335, filed on Nov. 6, 1998, now Pat. No. 6,152,937.

(51) Int. Cl.$^7$ ............................................. A61B 17/08
(52) U.S. Cl. ................................... 606/153; 606/151
(58) Field of Search ............................ 606/153, 151, 606/213, 215, 99, 219, 220, 224; 623/1.11

(56) References Cited

U.S. PATENT DOCUMENTS

| | | | |
|---|---|---|---|
| 4,214,587 A | 7/1980 | Sakura, Jr. ............... | 128/334 R |
| 4,503,569 A | 3/1985 | Dotter ............................. | 3/1.4 |
| 4,592,754 A | 6/1986 | Gupte et al. ................... | 623/1 |
| 4,617,932 A | 10/1986 | Kornberg ................. | 128/334 R |

(List continued on next page.)

FOREIGN PATENT DOCUMENTS

| | | | | |
|---|---|---|---|---|
| AU | 670239 | 1/1994 | ............ | A61F/2/06 |
| EP | 539237 A1 | 4/1993 | ............ | A61F/2/06 |
| EP | 0 637 454 A1 | 2/1995 | ............ | A61M/25/10 |
| EP | 0 680 734 A2 | 11/1995 | ............ | A61F/2/06 |
| EP | 0 684 022 A2 | 11/1995 | ............ | A61F/2/06 |
| EP | 0 701 800 A1 | 3/1996 | ............ | A61F/2/06 |
| EP | 0 712 614 A1 | 5/1996 | ............ | A61F/2/06 |
| EP | 0 732 088 A2 | 9/1996 | ............ | A61F/2/06 |
| EP | 0 732 089 A2 | 9/1996 | ............ | A61F/2/06 |
| GB | 489316 A | 7/1938 | | |
| GB | 2269104 A | 2/1994 | ............ | A61F/2/06 |
| WO | WO 89/08433 | 9/1989 | ............ | A61F/2/04 |
| WO | WO 93/00868 | 1/1993 | ............ | A61F/2/06 |
| WO | WO 93/20757 | 10/1993 | ........... | A61B/17/11 |
| WO | WO 94/01056 | 1/1994 | ............ | A61F/2/04 |
| WO | WO 95/21592 | 8/1995 | ............ | A61F/2/06 |
| WO | WO 96/14808 | 5/1996 | ............ | A61F/2/02 |
| WO | WO 96/18361 | 5/1996 | ............ | A61F/2/06 |
| WO | WO 96/22745 | 8/1996 | ............ | A61F/2/06 |
| WO | WO 96/25897 | 8/1996 | ............ | A61F/2/06 |
| WO | WO 97/13463 | 4/1997 | ........... | A61B/17/00 |
| WO | WO 97/13471 | 4/1997 | ........... | A61B/19/00 |
| WO | WO 98/02099 | 1/1998 | ........... | A61F/17/00 |
| WO | WO 98/19629 | 5/1998 | ............ | A61F/2/06 |
| WO | WO 98/38939 | 9/1998 | ........... | A61B/19/00 |
| WO | WO 98/38941 | 9/1998 | ........... | A61B/19/00 |
| WO | WO 98/38942 | 9/1998 | ........... | A61B/19/00 |

*Primary Examiner*—Julian W. Woo
(74) *Attorney, Agent, or Firm*—Fish & Neave; Robert R. Jackson; Denise Bergin

(57) ABSTRACT

A medical graft connector for connecting an end of a tubular graft conduit to a side wall of a patient's existing tubular body conduit via an aperture in the side wall thereof has a first plurality of fingers configured to engage an interior surface of the side wall of the existing conduit. A second plurality of fingers is configured to engage an exterior surface of the side wall of the existing conduit. A third plurality of fingers is received in an interior lumen of the graft conduit, and a fourth plurality of fingers is configured to pierce the graft conduit. The connector is radially deformable between a first size and a second size.

4 Claims, 20 Drawing Sheets

U.S. PATENT DOCUMENTS

| | | | |
|---|---|---|---|
| 4,665,906 A | 5/1987 | Jervis .................... 128/92 YN |
| 4,787,899 A | 11/1988 | Lazarus .......................... 623/1 |
| 5,104,399 A | 4/1992 | Lazarus .......................... 623/1 |
| 5,122,156 A | 6/1992 | Granger et al. ............. 606/219 |
| 5,135,467 A | 8/1992 | Citron .......................... 600/16 |
| 5,207,695 A | 5/1993 | Trout, III .................... 606/153 |
| 5,211,658 A | 5/1993 | Clouse .......................... 623/1 |
| 5,211,683 A | 5/1993 | Maginot .................... 128/898 |
| 5,275,622 A | 1/1994 | Lazarus et al. ................ 623/1 |
| 5,304,220 A | 4/1994 | Maginot ........................ 623/1 |
| 5,316,023 A | 5/1994 | Palmaz et al. ............. 128/898 |
| 5,354,336 A | 10/1994 | Kelman et al. ................ 623/6 |
| 5,366,462 A | 11/1994 | Kaster et al. ............... 606/153 |
| 5,387,235 A | 2/1995 | Chuter .......................... 623/1 |
| 5,397,345 A | 3/1995 | Lazarus ........................ 623/1 |
| 5,397,355 A | 3/1995 | Marin et al. .................. 623/12 |
| 5,443,497 A | 8/1995 | Venbrux ........................ 623/1 |
| 5,452,733 A | 9/1995 | Sterman et al. ............. 128/898 |
| 5,456,712 A | 10/1995 | Maginot ........................ 623/1 |
| 5,489,295 A | 2/1996 | Piplani et al. ................. 623/1 |
| 5,507,769 A | 4/1996 | Marin et al. ................. 606/198 |
| 5,522,880 A | 6/1996 | Barone et al. ................. 623/1 |
| 5,545,214 A | 8/1996 | Stevens ........................ 623/2 |
| 5,562,728 A | 10/1996 | Lazarus et al. ................ 623/1 |
| 5,617,878 A | 4/1997 | Taheri ........................ 128/898 |
| 5,676,670 A | 10/1997 | Kim ........................... 606/108 |
| 5,695,504 A | 12/1997 | Gifford, III et al. ......... 606/153 |
| 5,843,164 A | 12/1998 | Frantzen et al. ................ 623/1 |
| 5,843,170 A | 12/1998 | Ahn .............................. 623/1 |
| 5,843,175 A | 12/1998 | Frantzen ........................ 623/1 |
| 5,921,995 A | 7/1999 | Kleshinski ................... 606/153 |
| 5,976,178 A | 11/1999 | Goldsteen et al. ............. 623/1 |
| 6,013,190 A | 1/2000 | Berg et al. ..................... 216/34 |
| 6,026,814 A | 2/2000 | LaFontaine et al. ......... 128/898 |
| 6,035,856 A | 3/2000 | LaFontaine et al. ......... 128/898 |
| 6,036,702 A | 3/2000 | Bachinski et al. .......... 606/153 |
| 6,193,734 B1 | 2/2001 | Bolduc et al. ............... 606/163 |

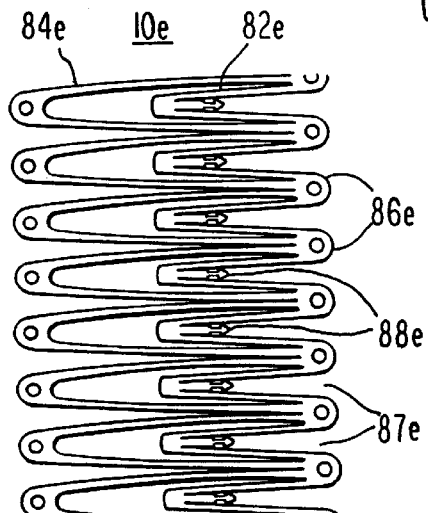
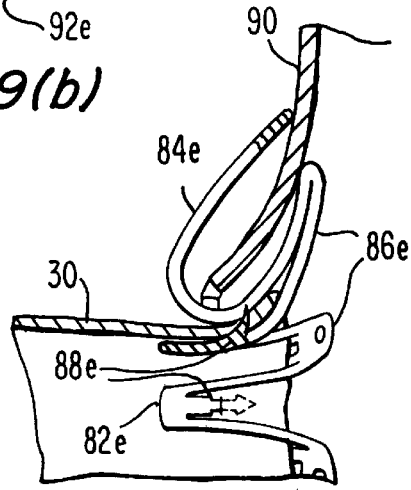
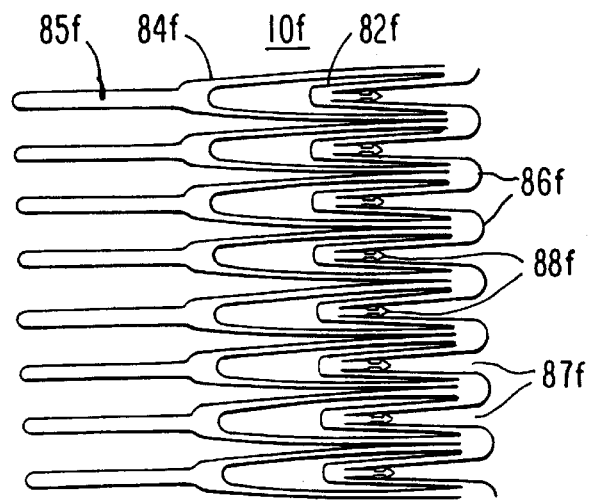
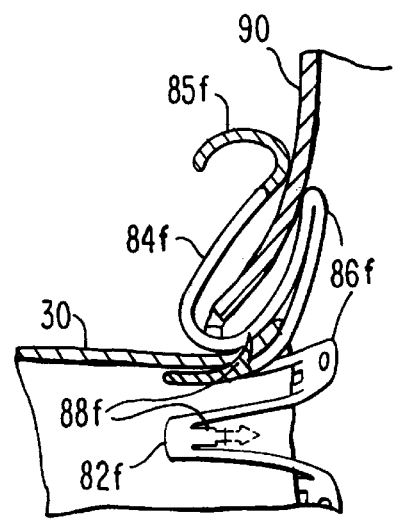

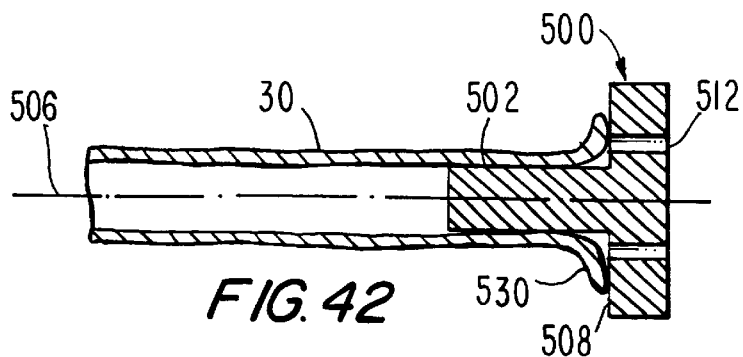
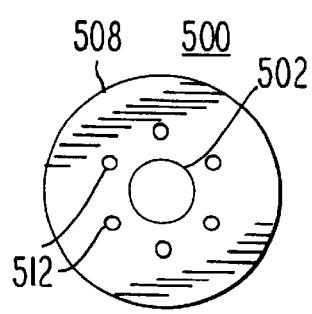
FIG. 42
FIG. 43
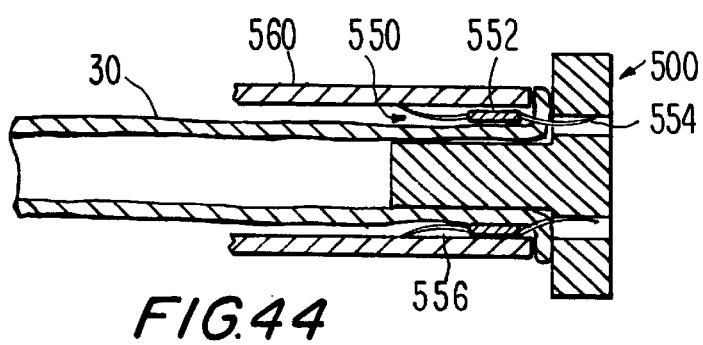
FIG. 44
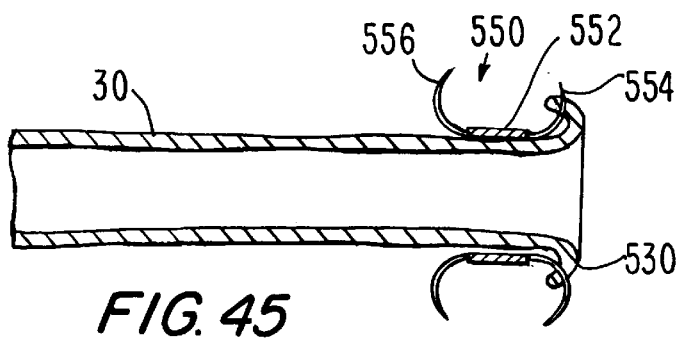
FIG. 45
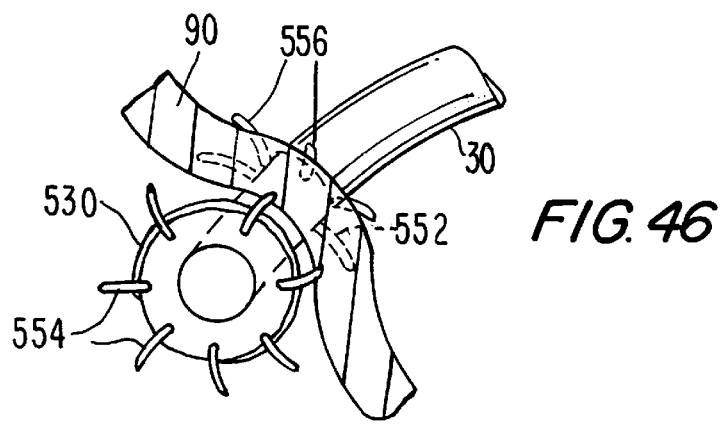
FIG. 46

MEDICAL GRAFT CONNECTOR AND METHODS OF MAKING AND INSTALLING SAME

This is a division of application Ser. No. 09/187,335, filed Nov. 6, 1998, (now U.S. Pat. No. 6,152,937), which is hereby incorporated by reference herein in its entirety.

BACKGROUND OF THE INVENTION

This invention relates to structures that can be used to make connections between tubular medical grafts and a patient's tubular body conduits. The invention also relates to methods for making and using the structures mentioned above.

Tubular grafts are frequently needed in medical procedures. For example, a coronary bypass procedure may involve the installation of a tubular graft between an aperture that has been formed in the side wall of the aorta and an aperture that has been formed in the side wall of a coronary artery downstream from an occlusion or blockage in that artery. Each end of the graft must be connected to the side wall of either the aorta or the coronary artery. Each such connection must extend annularly around the associated end of the graft conduit and be fluid-tight so that no blood will leak out. One common way to produce such connections is by suturing. It will be appreciated, however, that making such connections by suturing can be extremely difficult, time-consuming, and dependent on the skill of the physician for the quality of the results. There is also increasing interest in less invasive procedures which tend to impose constraints on the physician's access to the sites at which graft connections must be made and thereby make it more difficult or even impossible to use suturing to make such connections (see, for example, Goldsteen et al. U.S. Pat. No. 5,976,178, Sullivan et al. U.S. Pat No. 6,120,432, and published PCT patent application WO 98/55027, all of which are hereby incorporated by reference herein in their entireties).

Various types of mechanical connectors have been developed to reduce or eliminate the need for suturing, but improvements are constantly sought for such mechanical connectors with respect to considerations such as ease and speed of use, ease of manufacture, strength and permanence of the resulting connection, etc. A connector, including methods for making and installation thereof, is disclosed in published PCT patent application WO 99/38454, and is incorporated by reference in its entirety herein.

In view of the foregoing, it is an object of this invention to provide improved and simplified graft connectors for connecting two tubular structures without the use of sutures.

It is still another object of this invention to provide improved and simplified methods of making structures that can be used as medical graft connectors.

It is yet another object of this invention to provide improved and simplified methods for installing medical graft connectors.

SUMMARY OF THE INVENTION

These and other objects of the invention are accomplished in accordance with the principles of the invention by providing a connector which may be attached to two tubular structures without the use of sutures or other attachment means. The connector is preferably formed by using a highly elastic material such as nickel and titanium alloy (nitinol) metal. A first plurality of fingers is configured to engage an interior surface of the side wall of the existing conduit. A second plurality of fingers is configured to engage an exterior surface of the side wall of the existing conduit. A third plurality of fingers is received in an interior lumen of the graft conduit, and a fourth plurality of fingers is configured to pierce the graft conduit. The connector is radially deformable between a first size and a second size.

In a preferred embodiment, the pluralities of fingers are substantially radially aligned with respect to a longitudinal axis of the connector. The first and second pluralities of fingers may be resiliently deformable towards parallelism with the longitudinal axis of the connector. A substantially "U"-shaped configuration may be defined by adjacent ones of the first and second plurality of fingers when viewed from a plane extending radially out from a longitudinal axis of the connector.

To install the graft connector in a patient, a tubular graft conduit is attached to the connector. The first and second pluralities of fingers of the connector may be deflected inwardly toward parallelism with the longitudinal axis. The connector and graft conduit may be inserted in a delivery apparatus, which may maintain the fingers in their substantially axially extending condition. The delivery apparatus may then be inserted through the aperture in the side wall of the patient's tubular body conduit to which the end of the graft conduit is to be attached. The delivery apparatus is manipulated such that restraint is removed from the fingers of the connector. This permits the fingers to spring out to engage the tissue structure to which the connection is to be made. The delivery may be performed by passing the delivery structure intraluminally within the patient's tubular body conduit and through the wall of the body conduit to outside the conduit.

Further features of the invention, its nature and various advantages will be more apparent from the accompanying drawings and the following detailed description of the preferred embodiments.

BRIEF DESCRIPTION OF THE DRAWINGS

FIG. 19(a) is a planar representation similar to FIG. 2, illustrating another embodiment of the component of FIGS. 1–3.

FIG. 19(b) is an enlarged view of a portion of the component of FIG. 19(b).

FIG. 19(c) is a side view in partial cross-section similar to FIG. 14, illustrating the component of FIG. 19(a) after processing and installation in the patient.

FIG. 20(a) is a planar representation similar to FIG. 2, illustrating another embodiment of the component of FIGS. 1–3.

FIG. 20(b) is a side view in partial cross-section similar to FIG. 14, illustrating the component of FIG. 20(a) after processing and installation in the patient.

FIG. 42 is a simplified sectional view of a graft conduit, and an apparatus for installing a component on the graft conduit.

FIG. 43 is a simplified elevational view of the apparatus of FIG. 42.

FIG. 44 is a sectional view similar to FIG. 42, illustrating a stage in the installation of a component on the graft conduit.

FIG. 45 is a view similar to FIG. 44, illustrating a component in accordance with the invention installed in the graft conduit.

FIG. 46 is a simplified perspective view in partial cross-section, illustrating the graft conduit and component of FIGS. 42–43 installed in the tubular body conduit.

DETAILED DESCRIPTION OF THE PREFERRED EMBODIMENTS

Figure 1:
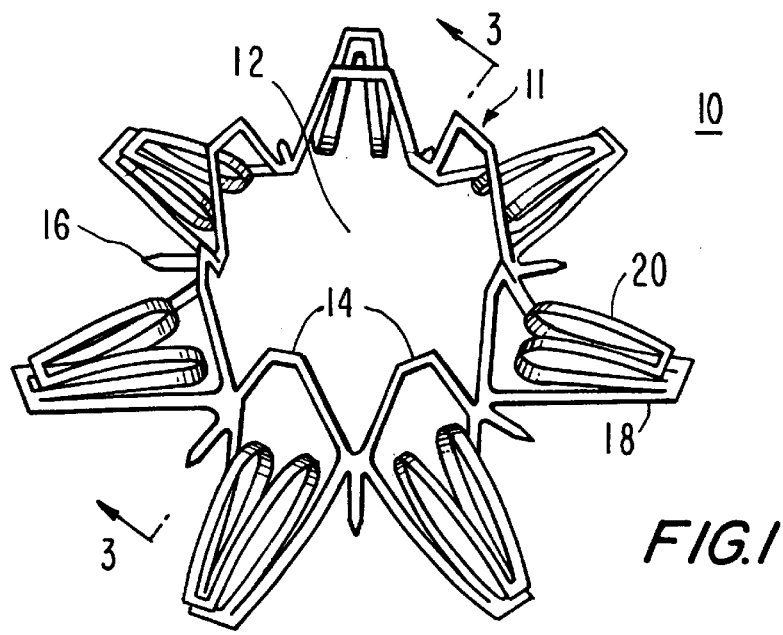
FIG. 1 is a perspective view of an illustrative embodiment of a component of this invention.

FIG. 1 illustrates a preferred embodiment of a connector 10 for use in connecting an end portion of a tubular graft conduit to a side wall of a patient's tubular body conduit. In order to facilitate the end-to-side anastomosis of two tubular body conduits, connector 10 is formed with a substantially radial configuration having a band portion 11 defining a central aperture 12 about which a plurality of components, or fingers, are oriented radially and axially outward from the band portion. The band 11 is configured for coaxial mounting with respect to the end portion of a graft conduit, and the fingers are configured to engage the side wall of a tubular body conduit through an aperture in that side wall. In the preferred embodiment, the band 11 is composed of a plurality of internal struts 14. The internal struts 14 are configured to engage one side of the wall of a graft conduit. Engagement members 16 extend radially outward and assist to secure the graft conduit to the connector 10, as will be described in greater detail below. A plurality of internal opposition fingers 18 are positioned adjacent a plurality of external opposition fingers 20 and extend radially and axially outward from an end portion of the band 11. The internal 18 and external fingers 20 are configured to engage both the inside and the outside wall of a second tubular conduit, typically a body conduit. As described in greater detail below, connector 10 is preferably fabricated from a single piece of material as a single, integral unit.

Figure 2:
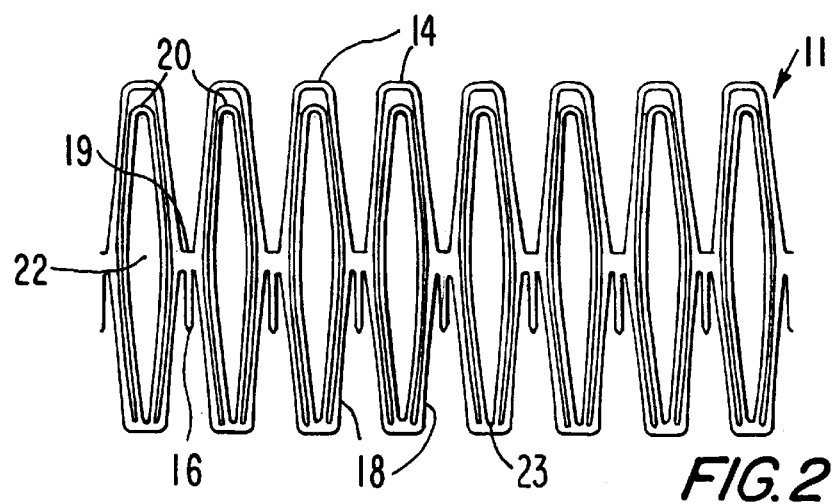
FIG. 2 is a simplified planar representation of the component of FIG. 1.
Figure 3:
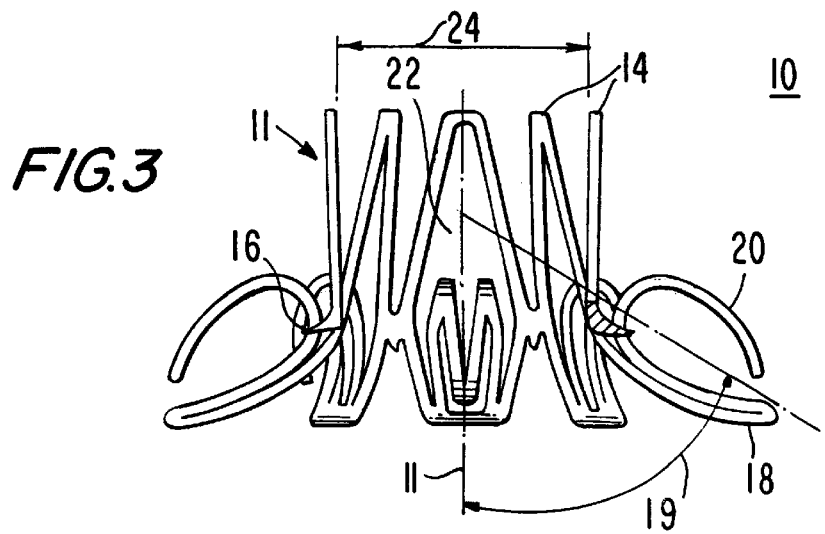
FIG. 3 is a side view in partial cross-section of the FIG. 1 component taken through lines 3—3 of FIG. 1.

FIG. 2 illustrates a planar representation of the connector of this invention shown in FIGS. 1 and 3. Component 10 may be formed from a sheet of material, which is preferably highly elastic. A particularly preferred material is nickel titanium alloy (nitinol) metal, but other materials such as stainless steel or thermoplastics may be used instead if desired. The starting sheet may have any length, diameter, and wall thickness suitable for the intended use of the finished connector. For example, the thickness of the sheet and the length of the struts and opposition fingers may be determined by the size of the body conduits joined or the pressure of fluids passing therethrough. For use as a cardiac bypass graft connector, for example, band 11 may have a nominal diameter 24 of about 4.0 millimeters, a wall thickness of about 0.003 inches, and a length of about 7.0 millimeters. It will be understood, however, that these specific dimensions are only exemplary, and that any other dimensions can be used instead if desired.

A first step in manufacturing component 10 in accordance with the invention is to form the sheet into a cylindrical tube. The next step involves cutting or machining the tube. The following cutting steps may be performed simultaneously, or in any order deemed appropriate by one skilled in the art. The axial end portions of the sheet are substantially axially cut to provide a plurality of fingers. Substantially axial "U"-shaped cuts may be made at spaced intervals in order to provide a separation between the fingers. In this embodiment, the internal opposition fingers 18 and engagement members 16 are formed by such cutting and extend substantially axially from the band portion 11. As will be described below, internal opposition fingers 18 and engagement members 16 define the distal portion of the connector.

A second set of fingers is cut from the band portion 11, i.e., a medial portion of the sheet, or tube. More particularly, a series of substantially axial "U"-shaped cuts are made in the sheet to define external opposition fingers 20. Each "U"-shaped cut includes two elongated axial cuts which may extend from one axial end portion of the sheet to the other end portion, and a shorter transverse cut adjacent one end portion of the sheet to provide the "U" configuration. (The cut may remove material from the sheet, as shown in the FIG.) The external opposition finger 20 thus defined has an end portion 23 integral with an internal opposition finger 18. Fingers 20 are substantially longer than fingers 18 in order to be partially coextensive with fingers 18 (see FIG. 3) and to provide contact surfaces with both the graft conduit and the body conduit, as will be described below. Each external opposition finger 20 is "U"-shaped in the plan view due to a medial aperture 22 defined in the center of each of the fingers 20.

Thus, a portion of the band 11 is removed by the formation of the external opposition fingers 20. Further material is removed from the band 11 by a series of substantially axial cuts to create internal struts 14 at the opposite axial end from the cuts made to form fingers 18 and 16. Thus, band portion 11 has a substantially "zigzag" configuration for coaxial mounting with respect to the tubular graft portion, including struts 14 and intermediate strap portions 19 defined between each set of internal struts 14. The combination of the resiliency of the component material, axial cuts, "U"-shaped cuts, and apertures 22 allows radial contraction and expansion of the diameter 24 of band 11, and therefore of component 10, during delivery and deployment, as will be described in greater detail below.

The starting tube is machined into the configuration (represented as a plane in FIG. 2) by laser cutting, electron discharge machining (EDM), or etching. The machining may be performed either in the cylindrical tubular configuration or in the sheet configuration, depending upon the requirements of the materials and machining methods. Material not shown in FIG. 2 is subsequently removed from the starting sheet to provide the geometry shown in the FIG.

The next step is to deflect fingers on the machined tube to approximately the positions that are desired in the finished and installed connector. For example, FIG. 3 shows resilient fingers 20 and 18 extending radially and axially outward from an end portion of band 11. The machined tube is placed in a mold and heat-shaped into a geometry approximately that which the component 10 will assume after deployment. It will be appreciated that it may be desirable to deflect fingers 18 and 20 beyond their desired positions so that when they are substantially released during deployment, they will resiliently bear on the tissue in which the connector is installed in their effort to return to the positions to which they have been deflected in this step of their manufacture. The shape is retained after removing component 10 from the mold due to the properties of the NiTi material. The connector can be cooled to improve malleability to aid in positioning into the mold or during delivery. As can be clearly seen in the FIG., adjacent ones of fingers 18 and 20 likewise define a "U"-shaped configuration when viewed from a plane extending radially out from the band portion 11. The "U" configuration may also form an angle 19 less than a right angle with the axis 11 (typically 20°–90°), as will be described in greater detail below. Connector 10 defines a nominal diameter 24. It is contemplated that nominal diameter 24 is selected to be marginally greater than the internal diameter of the graft conduit, such that the internal struts 14 bear on the interior of graft when they are positioned inside the graft. Apertures 22, as well as the resilient material selected for the connector 10, permit the expansion and reduction of the diameter from the nominal diameter 24.

Connector 10, subsequent to formation, above, is used to join a graft conduit and a tubular body conduit in an end-to-side anastomosis. The graft conduit may be a natural conduit (e.g., a relocated portion of the patient's tubular body tissue), an artificial conduit (e.g., of the type shown in above-mentioned U.S. Pat. No. 5,976,178), or a composite of natural and artificial conduits.

Figure 4:
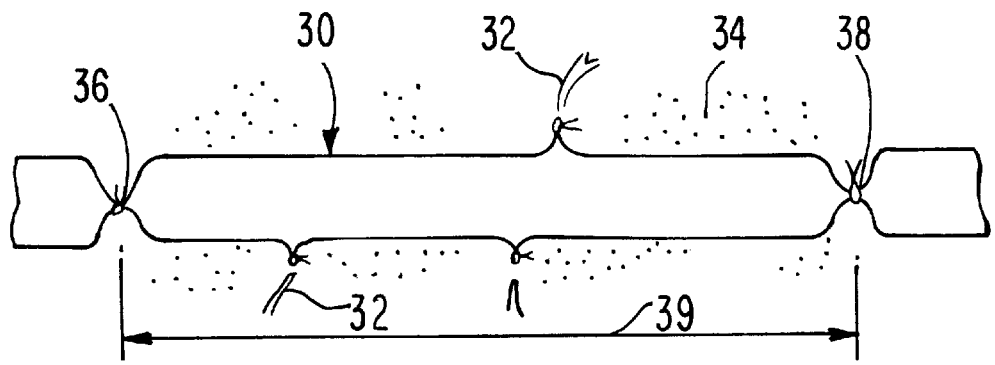
FIG. 4 is a simplified elevational view of a graft conduit, during a first stage of processing the body conduit.

FIGS. 4–7 show apparatus and methods to prepare, and in some cases, remove a body conduit for use as the graft conduit. FIG. 4 illustrates conduit 30 disposed within the body and typically serving as a conduit for fluid, e.g., blood. The conduit 30 has a plurality of side branches 32 for transporting fluid between the conduit 30 and the surrounding tissue 34. In an exemplary embodiment, the conduit 30 is an external jugular vein. A portion of the conduit is exposed. In this embodiment, approximately 15 cm of the vein is exposed. A first, or cranial location 36 is selected. A second, or caudal location 38 is likewise selected. The first 36 and second locations 38 are spaced apart by a length 39, e.g. 12 cm for use as a graft conduit in coronary artery bypass. The graft conduit 30 is ligated, clipped, or otherwise closed at the first 36 and second locations 38. The side branches 32 protruding from the vein body are subsequently ligated and cut.

Figure 5:
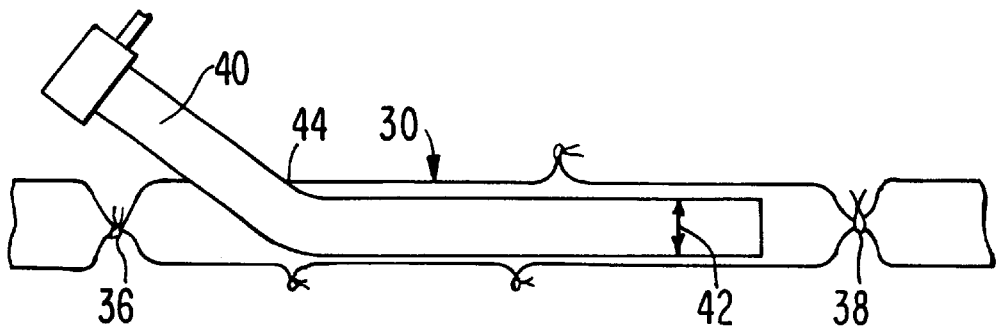
FIG. 5 is a view similar to FIG. 4, illustrating a subsequent stage of processing.

As illustrated in FIG. 5, an introducer 40, having a diameter 42 of approximately 3 French, is inserted into the graft conduit 30 at a point 44 slightly distal of the first location 36. The introducer 40 is advanced distally to a position adjacent the second location 38. An end portion of the introducer 40 remains outside the graft conduit 30.

Figure 6:
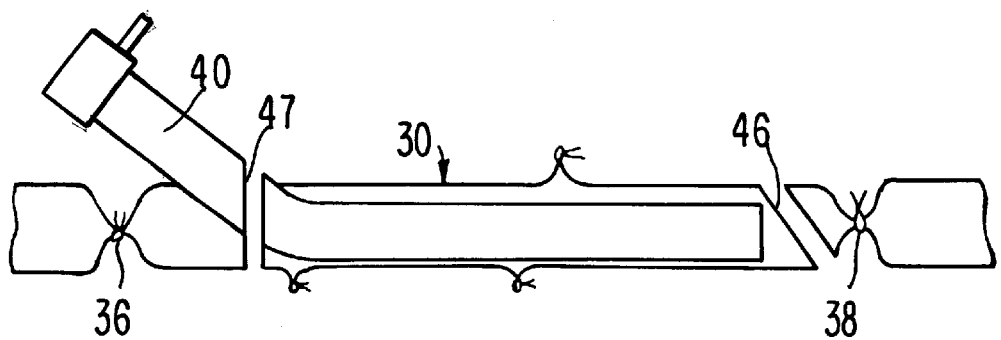
FIG. 6 is a view similar to FIG. 5, illustrating a further stage in such processing.
Figure 7:
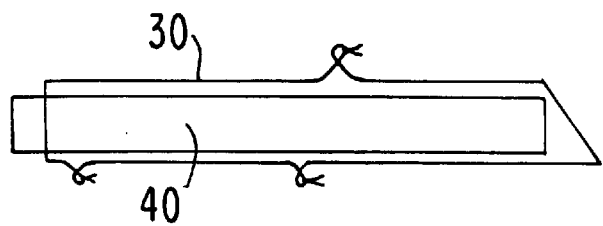
FIG. 7 is a simplified elevational view, illustrating the body conduit after the processing of FIGS. 4–6.

The conduit 30 is provided with a first cut 46 defining an oblique angle of approximately 45° with respect to the conduit axis adjacent the second location 38 (FIG. 6). It is contemplated that this procedure may be used for a conduit which is not entirely removed from its original location. For example, the internal mammary artery (IMA) is used as a blood source in coronary artery bypass procedures by cutting one end of the IMA and connecting that end to the coronary artery downstream of an occlusion by end-to-side anastomosis. A second cut 47 is made at approximately a 90° angle with respect to the axis adjacent the first location 36. This second cut 47 passes through both the graft 30 and introducer 40. The cut portion of the introducer 40 outside the graft conduit 30 is discarded. The graft 30 and introducer 40 are removed such that the introducer 40 remains within the graft 30 (FIG. 7), and both graft 30 and introducer 40 are placed in an appropriate solution. The graft 30 is to be used for connection to the side wall of the tubular body conduit.

Connector 10 may be installed to join two tubular conduits using several techniques. An exemplary apparatus 50 for installing connector 10 in the patient is illustrated in FIG. 8. Apparatus 50 may be used in minimally invasive surgical procedures, wherein an incision, access trocar or other small entry opening is provided in the patient's body. Such opening should be sized to permit insertion of the instrument 50 to the site wherein the anastomosis of the tubular conduits is to take place. Alternatively, apparatus 50 may be used in conventional surgical techniques where full access and direct visualization is appropriate. In addition, apparatus 50 may also be used in a procedure wherein connector 10 is deployed from inside the lumen of a body conduit to the outside thereof.

FIG. 8 illustrates apparatus 50 prior to the mounting of component 10 therein. Apparatus 50, includes a number of coaxial sleeves which are relatively axially slidable and angularly rotatable. Preferably, the sleeves are actuable by the physician from the proximal end portion of the instrument. An inner rod 52 is provided with a distal tip 54. An atraumatic end 59 of distal tip 54 may be curved or conical to facilitate insertion into an aperture in the side wall of a tubular body conduit. If the conduit is particularly delicate or susceptible to collapse, the distal tip may be provided with more gradual taper as deemed appropriate by the physician. Surrounding inner rod 52 is an intermediate sleeve 56. Likewise, surrounding intermediate sleeve 56 is an outer sleeve 58. At least the distal end portions of inner rod 52, intermediate sleeve 56, and outer sleeve 58 are preferably manufactured from a rigid material such a metal or a surgical grade plastic material. Locking mechanism 60 is provided to releasably secure inner rod 52 with respect to intermediate sleeve 56. Similarly, locking mechanism 62 releasably secures intermediate sleeve 56 with respect to outer sleeve 58. Locking mechanisms 60 and 62 may be manufactured in accordance with any type of mechanism known in the art, such as a releasable clamp or friction fitting, set screw, or bayonet mount. Locking mechanisms 60 and 62 are advantageously selected to maintain the small overall diameter of apparatus 50. Sheath 64 is provided to surround outer sleeve 58. Sheath 64, which also protects the graft conduit from damage during the anastomosis, may be fabricated from a flexible material, such as a polymer.

Figure 8A:
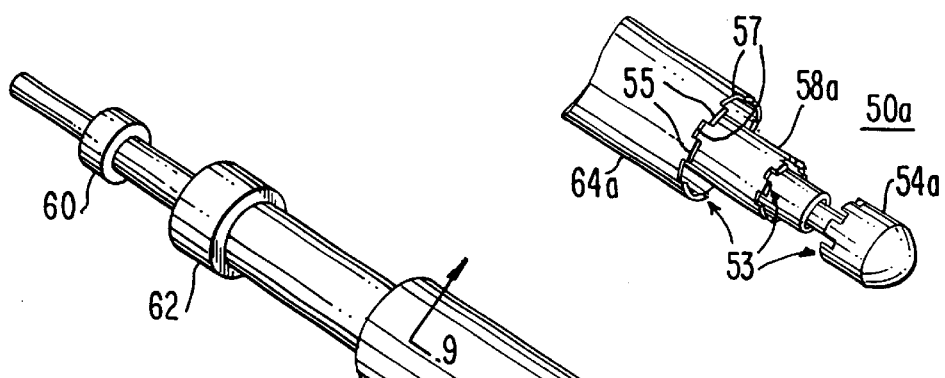
FIG. 8(a) is a partial perspective view, similar to FIG. 8, of an alternative embodiment of apparatus suitable for installing the component of FIG. 1.
Figure 8:
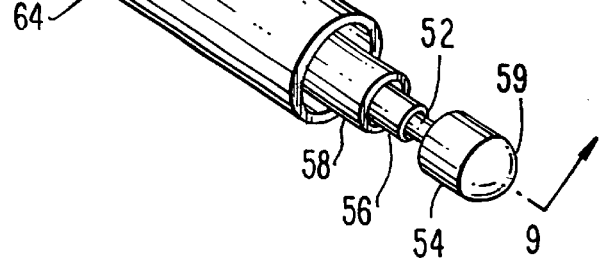
FIG. 8 is a perspective view of apparatus according to the invention which is suitable for installing the component of FIG. 1.

As illustrated in FIG. 8(a), apparatus 50a, substantially identical to apparatus 50, is provided with a crenelated configuration 53 on end portions of outer sheath 64a, outer sleeve 58a and distal tip portion 54a. The crenelated configuration 53 defines a series of alternating protrusions 55 and notches 57, which cooperate with fingers 14, 18 and 20 of component 10, as will be described in greater detail below. The various components of apparatus 50a are configured for both axial movement and angular rotation. It is contemplated that remote rotation of the components of apparatus 50a is enabled by various rotation devices, such as collars or knobs known in the art, provided at the proximal end of the device (not shown).

Figure 9:
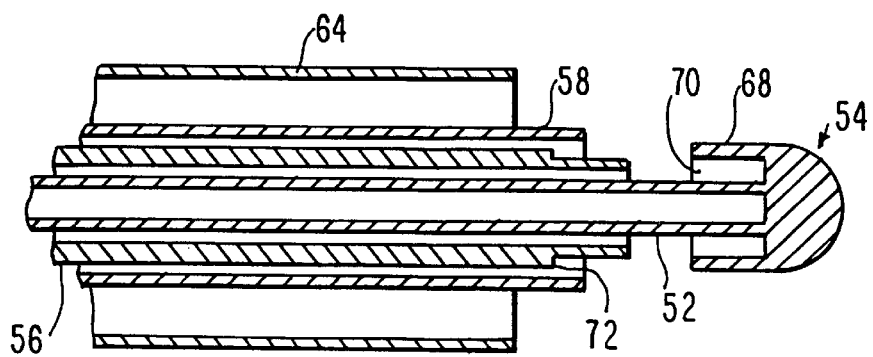
FIG. 9 is a simplified sectional view of the component of FIG. 8, taken along lines 9—9 of FIG. 8.

FIG. 9 further illustrates the relative positioning of the components of apparatus 50. Distal tip 54 is configured with a circumferential flange or collar 68 that defines an annular space 70 between collar 68 and inner rod 52. Annular space 70 stores the internal opposition fingers 18 of connector 10 during installations, as will be described below. Intermediate sleeve 56 has a circumferential shoulder portion 72 near the distal portion thereof to assist in positioning connector 10.

Figure 10:
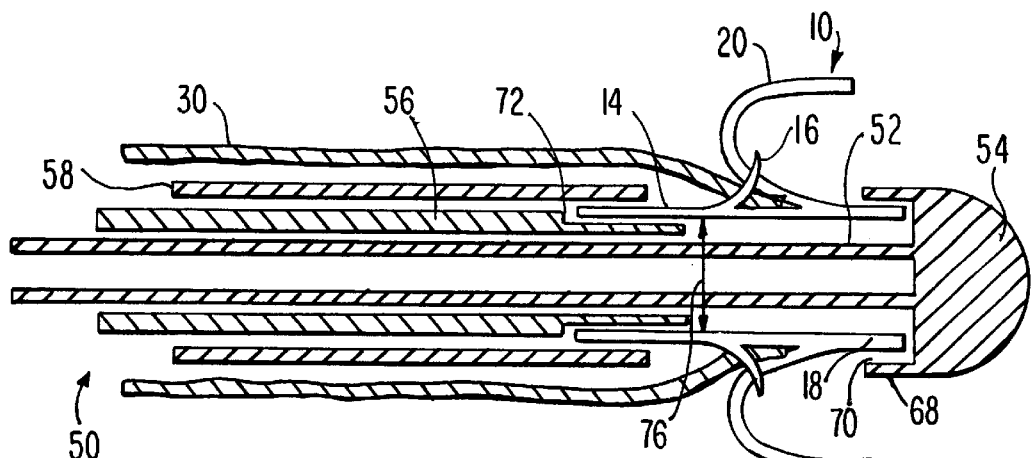
FIG. 10 illustrates the FIG. 9 apparatus with a graft conduit added so that the FIG. 1 component can be used as a connector for the graft conduit.

Connector 10 is mounted at the distal portion of instrument 50, as shown in FIG. 10. Component 10 is radially compressed for placement on intermediate sleeve 56. More particularly, the resilient characteristics of band portion 11 of connector 10 enable the nominal diameter 24 (see, FIG. 3) to be reduced to a smaller diameter 76 (FIG. 10). Internal opposition fingers 18 (shown in their relaxed curvilinear configuration in FIG. 3) are deflected radially inwardly toward parallelism with the longitudinal axis and retained in a substantially axial configuration within space 70 by collar 68. Internal struts 14 are maintained in position around intermediate sleeve 56 and in engagement with shoulder portion 72 by outer sleeve 58.

Graft conduit 30 is positioned coaxially over outer sleeve 58. Engagement members 16 are arrayed radially outwardly for engagement with the distal end portion of graft conduit 30. A space is defined between external opposition fingers 20 and internal opposition fingers 18. As illustrated in the FIG., the distal end portion of graft conduit 30 is positioned under external opposition fingers 20 and over internal opposition fingers 18. A sharpened end portion of member 16 pierces graft conduit 30 to securely restrain graft conduit 30 in place. Graft conduit 30, mounted between external opposition fingers 20 and internal opposition fingers 18 and held by engagement members 16 is secured to connector 10 without the need for sutures or other connection material. It is contemplated that additional connection material maybe used if the physician considers such reinforcement to be necessary.

Figure 11:
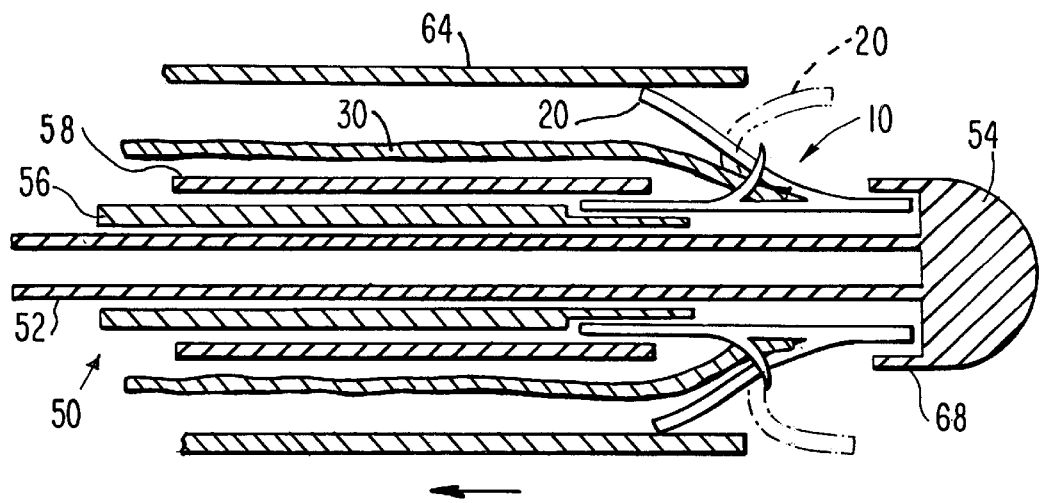
FIG. 11 is a simplified sectional view of the FIG. 9 apparatus with another component added to facilitate insertion in the patient.

As depicted in FIG. 11, sheath 64 is positioned over connector 10 and graft conduit 30 from the distal end portion of apparatus 50 toward the proximal end, as indicated by the arrow. The external opposition fingers 20 are deflected from their distally facing curve (illustrated in dashed lines) to a deflected, proximally facing configuration toward parallelism with the longitudinal axis and maintained in this configuration by sheath 64. The configuration illustrated in FIG. 11 is advantageous for insertion into a body conduit at the operative site. The retraction of the external opposition fingers 20 within sheath 64 and the atraumatic distal tip 54 minimizes the possibility of injuring adjacent tissue, which is particularly useful if apparatus 50 is used in a minimally invasive manner under endoscopic visualization.

Figure 12:
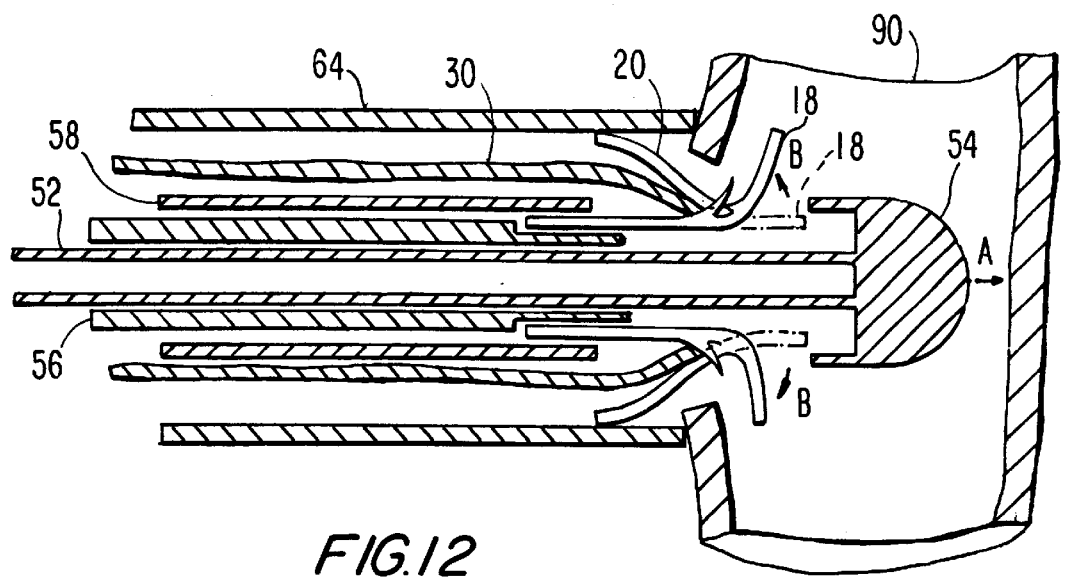
FIG. 12 is a simplified sectional view of the FIG. 11 apparatus, illustrating a stage in the installation the FIG. 1 component in a patient.

An aperture is made in the tubular body conduit 90 at the location where the anastomosis is desired. As illustrated in FIG. 12, distal tip 54 is inserted into conduit 90. Apparatus 50 is inserted into the aperture until sheath 64 is approximated with the wall of conduit 90 and engagement members 16 are positioned inside conduit 90. Locking mechanism 60 (see, FIG. 8) is released. Inner rod 52 and distal tip 54 are advanced distally (as indicated by arrow A), while intermediate sleeve 56 and outer sleeve 58 remain stationary. Once collar 68 has been advanced beyond the distal end of component 10, internal opposition fingers 18 are restored from the straightened configuration (illustrated in dashed lines) to a relaxed, curved configuration similar to that shown in FIG. 3 (indicated by arrows B). Internal opposition fingers 18 are approximated with the inner wall of conduit 90.

Subsequently, locking mechanism 62 (see, FIG. 8) is released and outer sleeve 58 may be withdrawn proximally while intermediate sleeve 56 remains stationary (as indicated by arrow C in FIG. 13). Internal struts 14 are released and engage the inner surface of graft conduit 30. Connector 10 expands radially outwardly in the direction shown by arrow D. This expansion allows connector 10 to place a compression stress, by pressing the wall of the graft conduit 30 against the aperture of conduit 90, to provide a secure hemodynamic seal. In addition, the increased radial dimension of connector 10 provides sufficient clearance for distal tip 54 to be withdrawn proximally from body conduit 90. Subsequently, inner rod 52 with distal tip 54 and intermediate 56 and outer sleeves 58 are removed proximally from the operative site.

Figure 14:
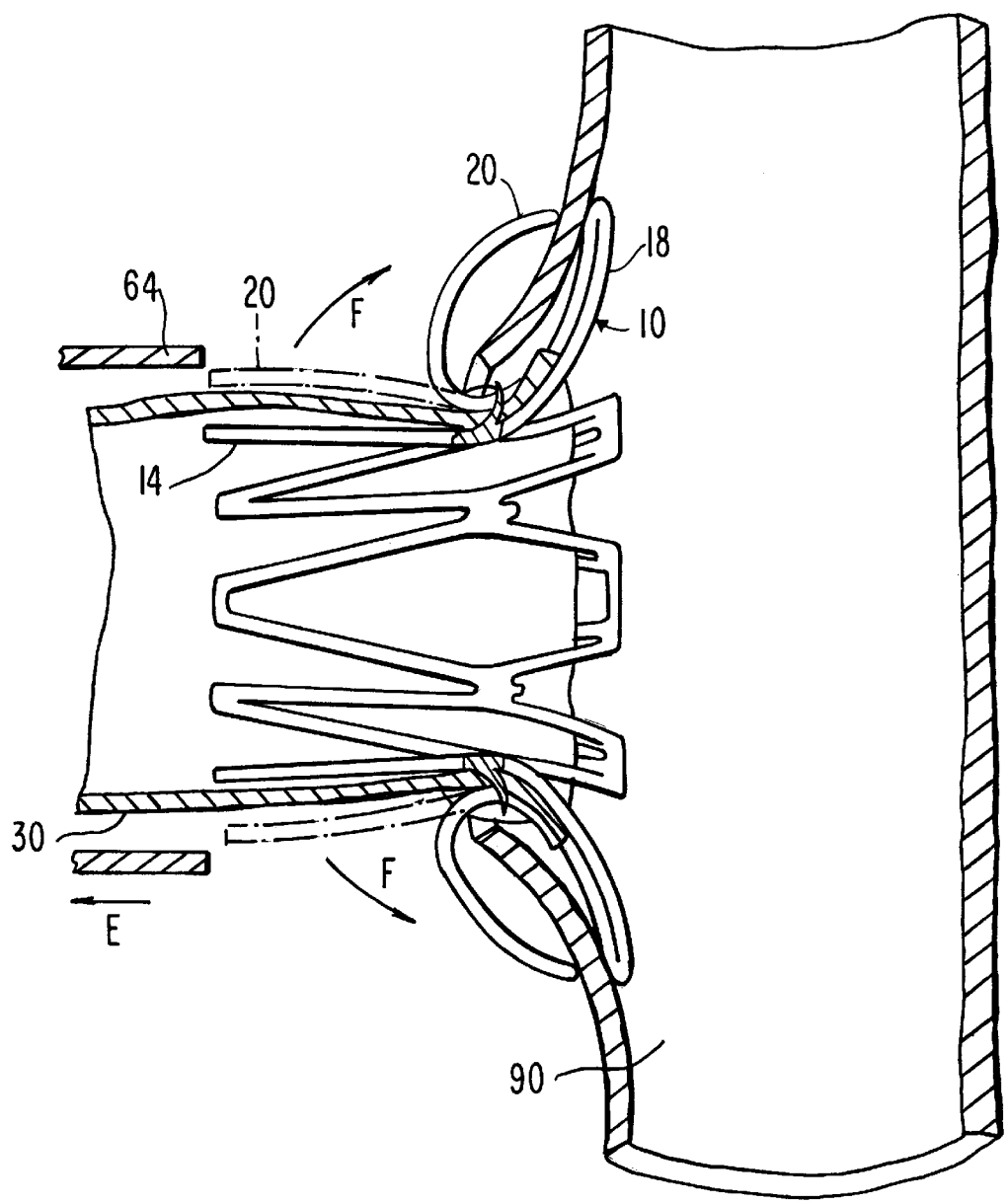
FIG. 14 is an enlarged view similar to FIG. 13, illustrating another further stage in the installation of the FIG. 1 component.

As illustrated in FIG. 14, sheath 64 is withdrawn proximally (in the direction of arrow E). When the distal end of sheath 64 clears the proximal end of external opposition fingers 20, the fingers 20 move as indicated by arrow F from the proximally extending, substantially straightened configuration (illustrated in dashed line) to a curvilinear configuration similar to that shown in FIG. 3. External opposition fingers 20 thus engage the outer surface of body conduit 90. As illustrated in the FIG., the angled "U"-shaped orientation of the inner 18 and external opposition fingers 20 cause the tissue of graft conduit 30 and body conduit 90 to assume a somewhat radially flared, "trumpet bell-shaped" configuration. This configuration improves the fluid seal between the graft 30 and body conduit 90 and promotes good fluid flow between these two elements. More particularly, the flared configuration reduces the abrupt transition in direction of fluid flowing from the graft to the body conduit. Consequently, turbulence in blood flow, which may result in injury to the vessel walls and thrombus or clotting, is reduced, and overall patency of the anastomosis is improved.

Figure 13:
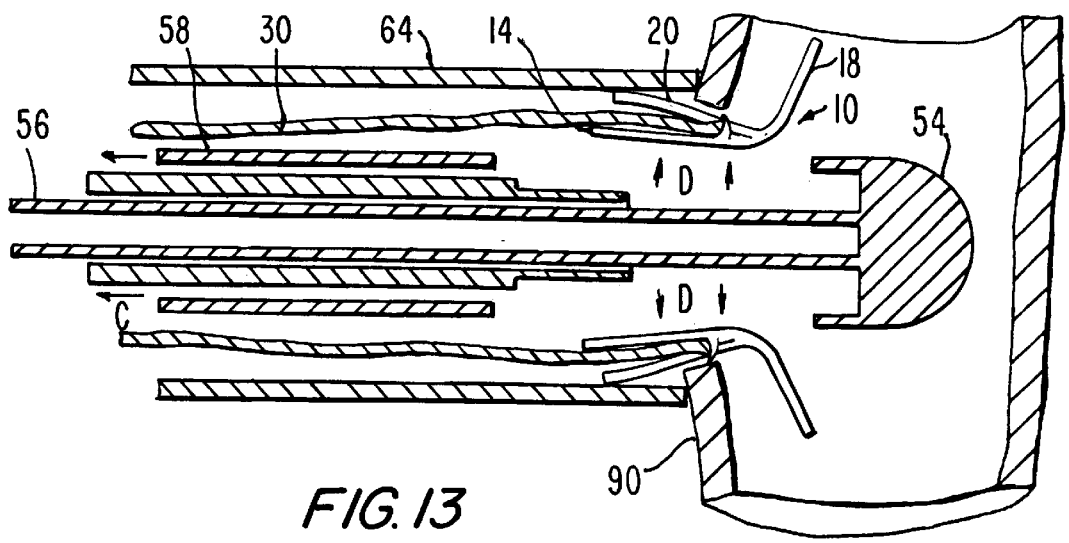
FIG. 13 is a view similar to FIG. 12, illustrating a further stage in the installation of the FIG. 1 component.

As described above with respect to FIG. 8(a), the crenelated configuration 53 permits the installation of component 10 with respect to the body conduit 90 by relative angular rotation of the components of apparatus 50a with respect to component 10, rather than by axial displacement, as with apparatus 50 (FIGS. 12–14). Component 10 is mounted with respect to apparatus 50a substantially as described with respect to apparatus 50 (FIGS. 10–11). However, protrusions 55 on outer sheath 64a retain fingers 20 in a substantially parallel configuration, protrusions 55 on outer sleeve 58a retain fingers 14 in a substantially parallel configuration, while protrusions 55 on distal tip 54a likewise retain fingers 18. Angular rotation of distal tip 54a with respect to component 10 aligns notches 57 with fingers 18, to thereby permit fingers 18 to approximate the curved configuration of FIG. 12. Similarly, angular rotation of outer sleeve 58a with respect to component 10 permits fingers 14 to displace radially outward as illustrated in FIG. 13. Finally, rotation of outer sheath 64a permits fingers 20 to resume the curved configuration (FIG. 14).

It is contemplated that the connector depicted above may be modified to conform to the requirements of a particular medical application. All of the connectors are designed to be deployed quickly and to connect the graft with the body conduit reliably. Furthermore, all of the connectors are substantially identical to connector 10 described above, with the modifications described below.

Figure 15A:
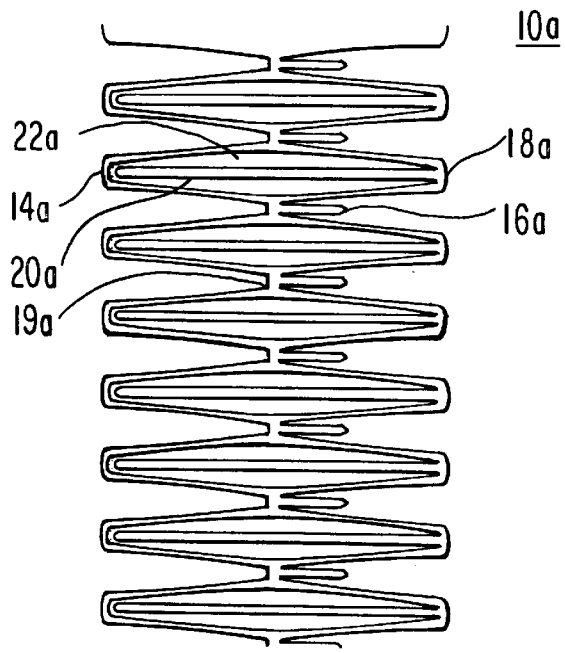
FIG. 15(a) is a planar representation similar to FIG. 2, illustrating another embodiment of the component of FIGS. 1–3.
Figure 15B:
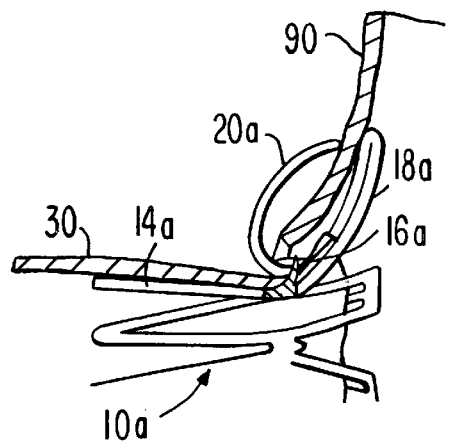
FIG. 15(b) is a side view in partial cross-section similar to FIG. 14, illustrating the component of FIG. 15(a) after processing and installation in the patient.

FIGS. 15(a) and 15(b) represent an alternative embodiment of the subject invention. FIG. 15(a) illustrates the machined section of connector 10a, which is substantially similar to connector 10. Connector 10a is provided with internal struts 14a, internal opposition fingers 18a, which are linked by intermediate straps 19a having engagement members 16a extending therefrom. Connector 10a is capable of expanding and contracting in diameter. External opposition fingers 20a are elongated solid fingers, and therefore are not provided with an aperture as is finger 20 of connector 10 (FIGS. 1–2). As FIG. 15(b) illustrates, connector 10a is deployed in body conduit 90 in a substantially identical manner to connector 10.

Figure 16A:
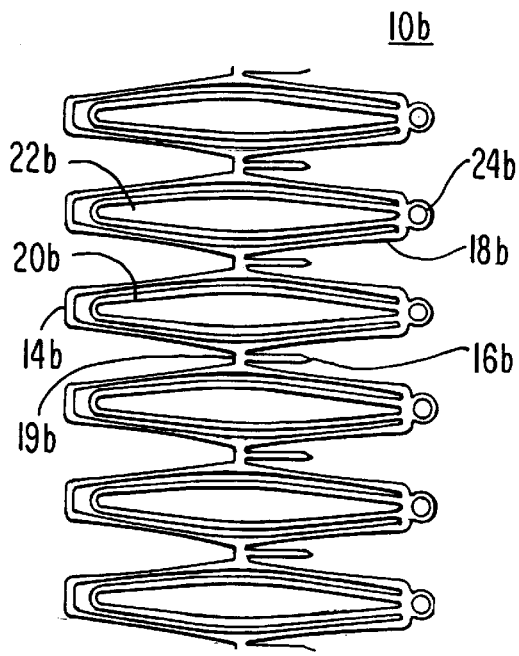
FIG. 16(a) is a planar representation similar to FIG. 2, illustrating another embodiment of the component of FIGS. 1–3.
Figure 16B:
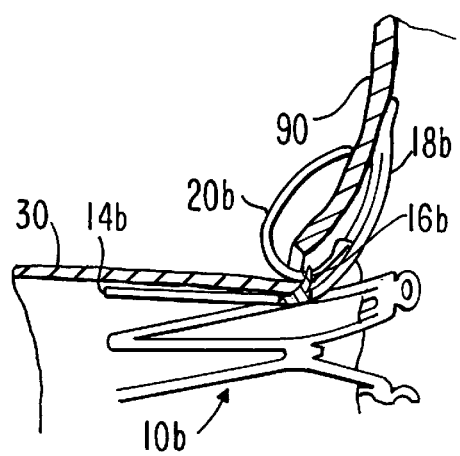
FIG. 16(b) is a side view in partial cross-section similar to FIG. 14, illustrating the component of FIG. 16(a) after processing and installation in the patient.

FIGS. 16(a) and 16(b) illustrate another embodiment of the subject invention. Connector 10b is substantially identical to connector 10. However, connector 10b is also provided with deployment loops 24b at the distal end portions of internal opposition fingers 18b. Deployment loops 24b may be used in connection with connector applying apparatus such as instrument 50 described above. Moreover, the deployment loops 24b may be engaged by positioning apparatus such as grasping hooks to position component 10b in a desired location. Deployment loops 24b may also serve as suture tie down points, should the physician determine that such sutures are necessary.

Figure 17A:
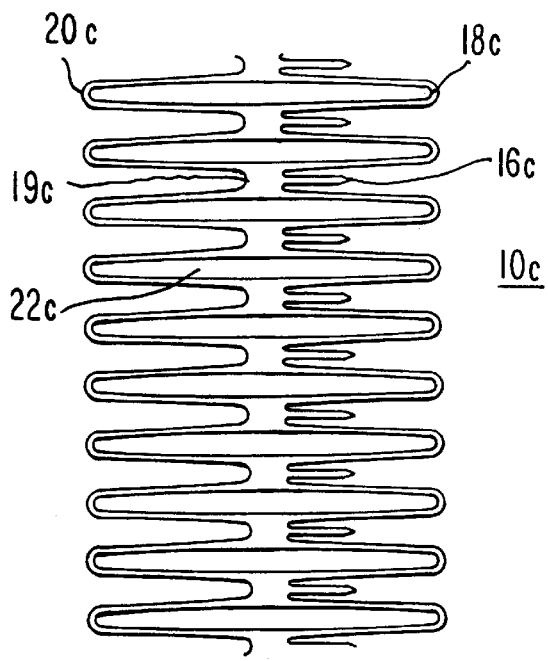
FIG. 17(a) is a planar representation similar to FIG. 2, illustrating another embodiment of the component of FIGS. 1–3.
Figure 17B:
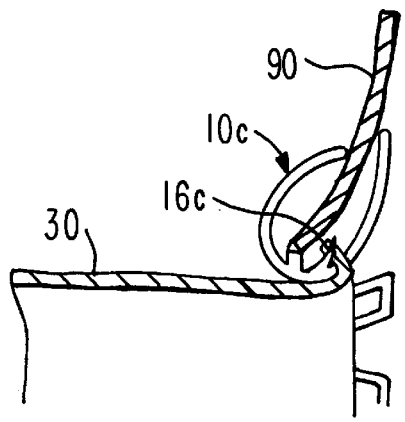
FIG. 17(b) is a side view in partial cross-section similar to FIG. 14, illustrating the component of FIG. 17(a) after processing and installation in the patient.

FIGS. 17(a) and 17(b) illustrate yet another embodiment of the subject invention. Connector 10c is positioned around the outer perimeter of the graft conduit, and is not provided with the internal struts 14 of connector 10. In plan view (FIG. 17(a)), the machined section of connector 10c is similar to that of connector 10. Connector 10c is provided with internal opposition finger 18c, intermediate strap portions 19c and engagement members 16c. However, external opposition fingers 20c extend from connection strap portions 19c rather than from the medial portions of internal opposition fingers 18c, as with connector 10. Apertures 22c are provided as with the previous embodiments to allow expansion and reduction of the diameter of the connector. As illustrated in FIG. 17(b), graft 30 is positioned inside connector 10c such that the graft is engaged by engagement members 16c and maintained in a radially flared configuration. Connector 10c may be installed substantially as described with respect to FIGS. 10–14, although it is contemplated that other installation methods may be used. More particularly, internal opposition finger 18c may be deflected into a flattened position by collar 68 of distal tip 54 (see similar FIGS. 10–11), and internal opposition fingers 20c deflected by outer sheath 64.

Figure 18A:
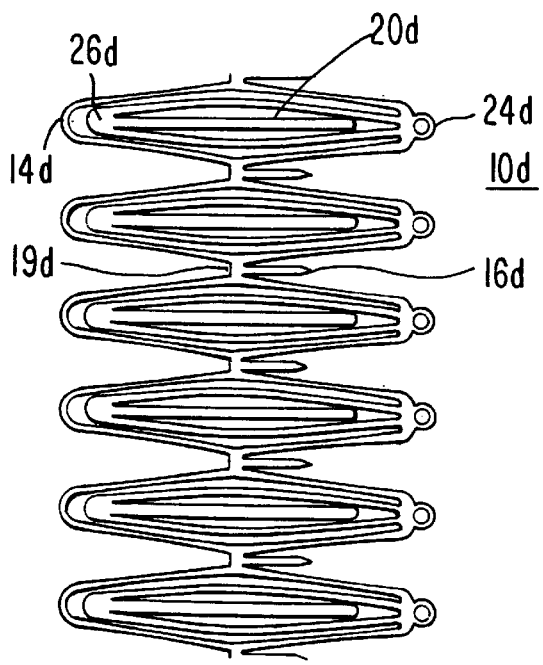
FIG. 18(a) is a planar representation similar to FIG. 2, illustrating another embodiment of the component of FIGS. 1–3.
Figure 18B:
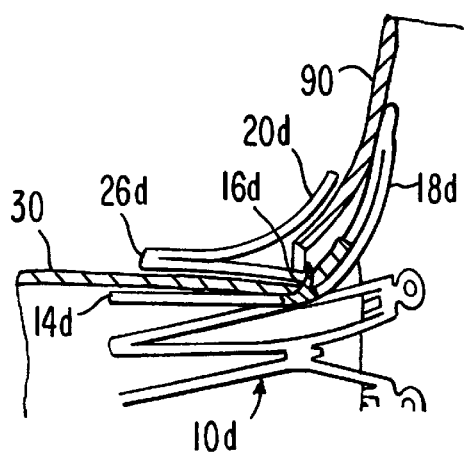
FIG. 18(b) is a side view in partial cross-section similar to FIG. 14, illustrating the component of FIG. 18(a) after processing and installation in the patient.

A further alternative embodiment of the subject invention is illustrated in FIGS. 18(a) and 18(b). In plan view, the machined section of connector 10d (FIG. 18(a)) is substantially similar to the section of connector 10b (FIG. 16(a)). However, external opposition finger 20d extends from an external support strut 26d. As illustrated in FIG. 18(b), the graft 30 is positioned between internal struts 14d and external struts 26d, and engagement members 16d are used to secure the graft 30 to connector 10d in a radially flared configuration. The connector 10d is held in place in body conduit 90 by internal opposition fingers 18d and external opposition fingers 20d. External opposition finger 20d has a flared configuration and conforms to the flared configuration of the body conduit opening. Connector 10d may be installed using apparatus such as instrument 50 substantially as described above with respect to FIGS. 8 and 9. More particularly, internal opposition finger 18d may be deflected into a flattened position by collar 68 of distal tip 54, and internal opposition fingers 20d deflected by outer sheath 64. Additional structure in apparatus 50 may be provided to cooperate with deployment loops 24d as illustrated in FIG. 18(a) above.

FIGS. 19(a), 19(b) and 19(c) illustrate an alternative embodiment in accordance with the subject invention. As the planar representation of FIG. 19(a) shows, connector 10e is provided with two sets of substantially "U"-shaped fingers, radial expansion members, or radial expansion members 82e and outer opposition fingers 84e. Each radial expansion member 82e is positioned with respect to an adjacent outer opposition finger 84e such that their respective end portions are joined at common locations, which form internal opposition fingers 86e, spaced apart by spacing 87e. This spacing 87e, in conjunction with the resilient characteristics of the material, permits the connector 10e to radially expand and contract, as will be described in greater detail below. In the preferred embodiment, radial expansion members 82e are smaller than outer opposition fingers 84e, although it is contemplated that radial expansion members 82e may be the same size or larger than outer opposition fingers 84e. At the vertex of each radial expansion member 82e is an engagement member 88e, which is configured to secure the graft conduit to the connector 10e. As illustrated in greater detail in FIG. 19(b), engagement member 88e has a sharpened tip 89e for piercing the tissue of the graft conduit. The pierced tissue is subsequently advanced past the tip 89e to a narrower neck portion 90e, positioned between shoulder portions 91e and 92e. Once the graft tissue has been positioned with respect to the neck portion 90e, the shoulder portions 91e and 92e prevent the tissue from slipping with respect to the engagement member 88e. Shoulder portion 92e inhibits the tissue from sliding off of engagement member 88e, whereas shoulder portion 91e inhibits the engagement member 88e from penetrating the tissue too deeply.

As illustrated in FIG. 19(c), connector 10e is formed such that outer opposition fingers 84e and internal opposition fingers 86e extend radially outward to form a substantially "U"-shaped configuration. Engagement members 88e are oriented radially outward. Connector 10e is installed with respect to conduit 90 and graft conduit 30 in a substantially similar manner to connector 10, as described with respect to FIGS. 10–14, above. With reference to FIG. 10, above, connector 10e may be mounted in a substantially similar manner, such that connector 10e is radially compressed when it is fitted over intermediate sleeve 56. Each radial expansion member 82e is positioned coaxially within outer sleeve 58, and each internal opposition finger 86e is held beneath collar 68 of distal tip portion 54. Graft conduit 30 is positioned over connector 10e such that engagement members 88e pierce the graft conduit and secure the graft tissue in the neck portion 90e of each engagement member 88e (FIG. 19(b)). With reference to FIG. 11, connector 10e is mounted in a substantially similar manner, such that each outer opposition finger 84e is deflected proximally and maintained in position by sheath 64.

When connector 10e is installed in body conduit 90 as shown in FIG. 19(c), connector 10e is permitted to return to a radially expanded configuration. Radial expansion members 82e contact and support graft conduit 30, which is secured by engagement members 88e. The end portion of graft conduit 30 is also positioned between radial expansion members 82e and outer opposition fingers 84e to provide a trumpet-shaped, or flared configuration. The wall of body conduit 90 is engaged by outer opposition fingers 84e and internal opposition fingers 86e, which have assumed an angled, substantially "U"-shaped configuration. This configuration, as described above, improves fluid flow and graft patency.

FIGS. 20(a) and 20(b) illustrate an alternative embodiment of the connector. Connector 10f is substantially similar to connector 10e. However, connector 10f is also provided with radiused portion 85f, which extends from outer opposition member 84f. As illustrated in FIG. 20(b), radiused portion 85f is formed with a curvature reversed from that given to outer opposition member 84f. The radiused portions 85f assist the surgeon in delivering and positioning the connector 10f by providing an atraumatic engagement structure for engaging a delivery system or existing body tubing, as will be described in greater detail below. Alternatively, portion 85f could be configured with any atraumatic surface, such as a beaded tip, which inhibits damage to existing body tubing during deployment.

Figure 21A:
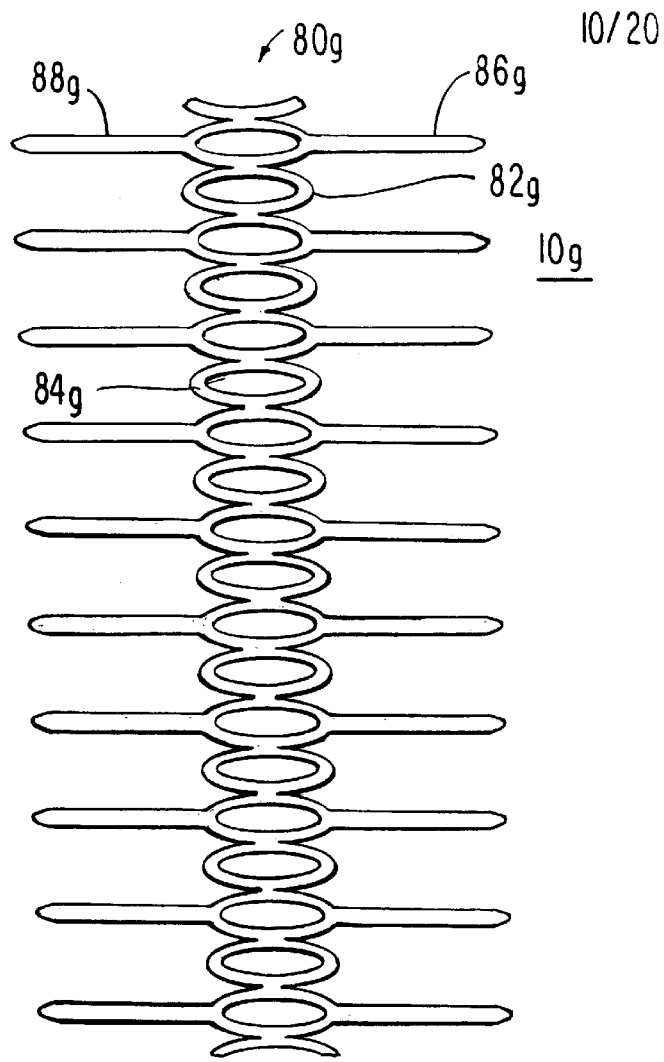
FIG. 21(a) is a planar representation similar to FIG. 2, illustrating another embodiment of the component of FIGS. 1–3.
Figure 21C:
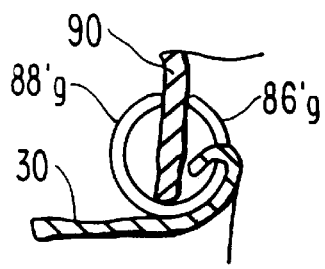
FIG. 21(c) is a side view similar to FIG. 21(b), illustrating an alternative embodiment.
Figure 21B:
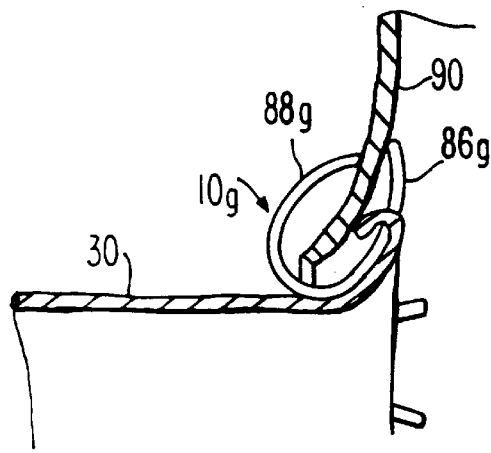
FIG. 21(b) is a side view in partial cross-section similar to FIG. 14, illustrating the component of FIG. 21(a) after processing and installation in the patient.

Yet another alternative embodiment of the subject invention is illustrated in FIGS. 21(a), 21(b) and 21(c). Connector 10g is provided with a band portion 80g, including a plurality of loops 82g connected at respective corners, each loop 82g defining an aperture 84g. A plurality of fingers is provided on both distal and proximal end portions of band 80g. Internal opposition fingers 86g extend from the distal side of each of alternating loops 82g. External opposition fingers 88g extend from the distal side of the same loop 82g as fingers 86g. As illustrated in FIG. 21(b), connector 10g is formed such that internal opposition fingers 86g and external opposition fingers 88g assume a "U"-shaped configuration to engage the wall of body conduit 90. As shown in the FIG., the "U"-shaped configuration of fingers 86g and 88g may be formed such that the conduit tissue assumes a radially flared bell-shaped configuration. Alternatively, fingers 86'g and 88'g may be given a "U"-shaped configuration which is symmetrical on both sides of the wall of conduit 90, as shown in FIG. 21(c). (It is contemplated that each of the embodiments of the subject invention may incorporate the symmetrical "U"-shaped configuration as well.)

Figure 22A:
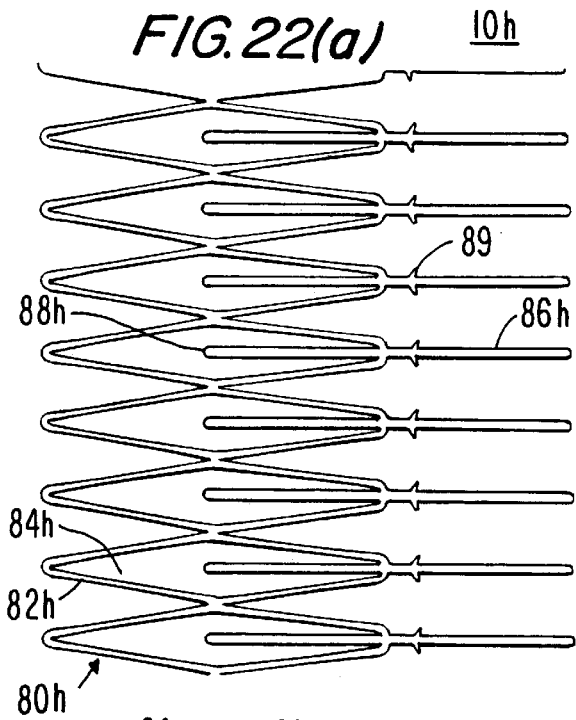
FIG. 22 (a) is a planar representation similar to FIG. 2, illustrating another embodiment of the component of FIGS. 1–3.
FIG. 22(b) is a side view in partial cross-section similar to FIG. 14, illustrating the component of FIG. 22 (a) after processing and installation in the patient.
Figure 22B:
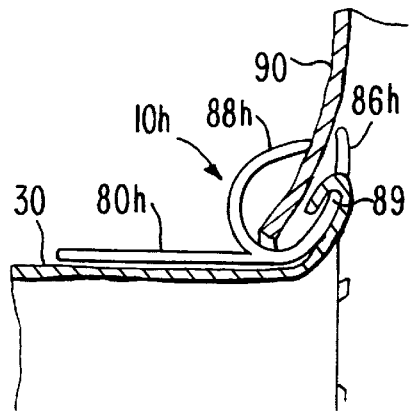

Yet another embodiment of the subject invention is represented in FIGS. 22(a) and 22(b). Connector 10h is provided with a band portion 80h having a plurality of loops 82h joined at their respective corners and defining apertures 84h therein. A plurality of fingers are provided on the distal portion of the loops. Both internal opposition fingers 86h and external opposition fingers 88h extend from the distal portion of the loops 82h. A shoulder portion, or barb 89, extends laterally from internal opposition finger 86h to secure the graft, as will be described below. As illustrated in FIG. 22(b), the graft 30 is placed inside formed connector 10h. Subsequently, the graft 30 is pierced by the internal opposition fingers 86h and maintained in a flared configuration. The barbs 89 on the internal opposition fingers 86h assist in the securing the graft 30 in position. Connector 10h is installed substantially as for connector 10g.

Figure 23A:
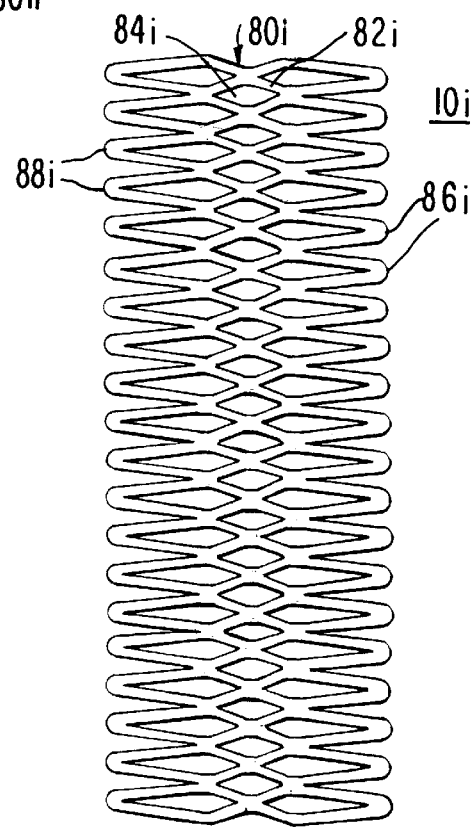
FIG. 23 (a) is a planar representation similar to FIG. 2, illustrating another embodiment of the component of FIGS. 1–3.
FIG. 23(b) is a side view in partial cross-section similar to FIG. 14, illustrating the component of FIG. 23 (a) after processing and installation in the patient.
Figure 23B:
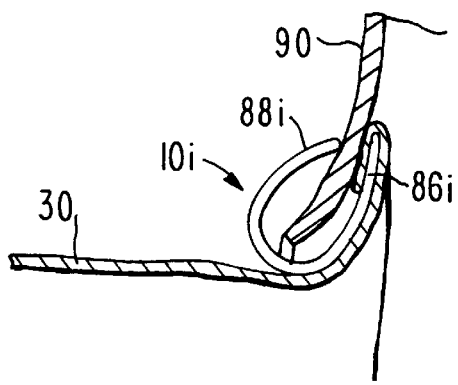

FIGS. 23(a) and 23(b) illustrate another embodiment of the subject invention. As for the connectors depicted in FIGS. 21–22 above, connector 10i is provided with a band section 80i including a plurality of loops 82i joined at respective corners and defining apertures 84i therein. Internal opposition fingers 86i and external opposition fingers 88i are substantially "U" shaped and have a pair of end portions. Internal opposition fingers 86i extend from the distal side of band section 80i. Likewise, external opposition fingers 88i extend from the proximal side of band section 80i. FIG. 23(b) illustrates the graft positioned inside connector 10i. The connector 10i is formed such that internal opposition fingers 88i form a flared configuration. The end portion of the graft is substantially expanded to assume this flared configuration and maintained in position by everting the end portion over the internal opposition fingers 86i without necessarily piercing the graft material or tissue. Thus, opposition fingers 86i may be provided with atraumatic tips. Internal 86i and external opposition fingers 88i are formed in the "U"-shaped configuration to grip the tissue of the body conduit 90 therebetween.

The connectors described above, particularly connector 10f (FIGS. 20(a) and 20(b)), are also suited for installation in the patient through percutaneous installation without the necessity to make surgical incisions in the patient near the operative site. Percutaneously deployed apparatus may be inserted into the lumen of a body conduit at a remote entry location and advanced intraluminally within the patient to the anastomosis site. Such percutaneous procedures are disclosed in commonly-assigned U.S. Pat. No. 5,976,178, and U.S. Pat. No. 6,036,702, which are incorporated by reference in their entirety herein.

Figure 24:
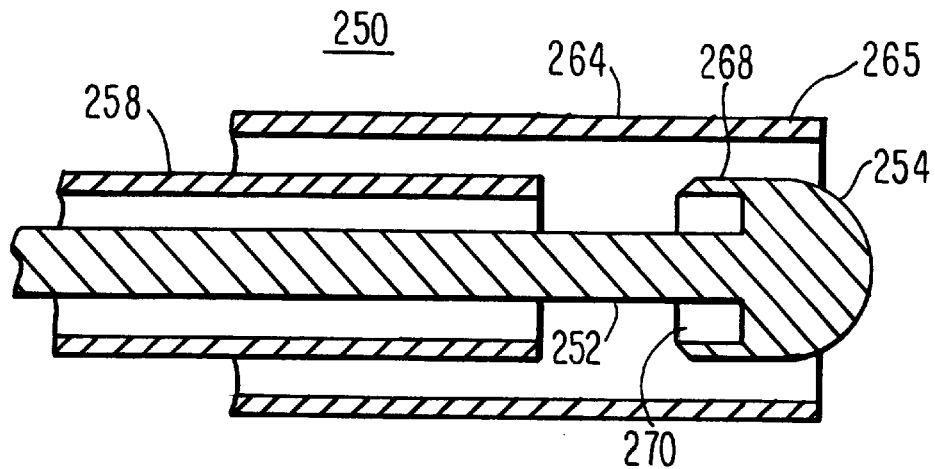
FIG. 24 is a cross-sectional view of an apparatus for installing the component of FIGS. 20(a)–20(b).

Apparatus for percutaneous installation of connector 10f is illustrated in FIG. 24, and denoted by reference number 250. Apparatus 250 may include an inner rod 252 (alternatively, an inner sleeve or sheath may be used), outer sleeve 258, and catheter or sheath 264. Inner rod or sheath 252, which has a distal tip 254, is substantially similar to inner rod 52 and distal tip 54, described above. Distal tip 254 has a circumferential flange, or collar 268, defining an annular space 270 between inner sleeve 252 and flange 268. An outer sleeve 258 is coaxially positioned around inner sleeve 252. Sheath 264 surrounds the entire assembly.

Figure 25:
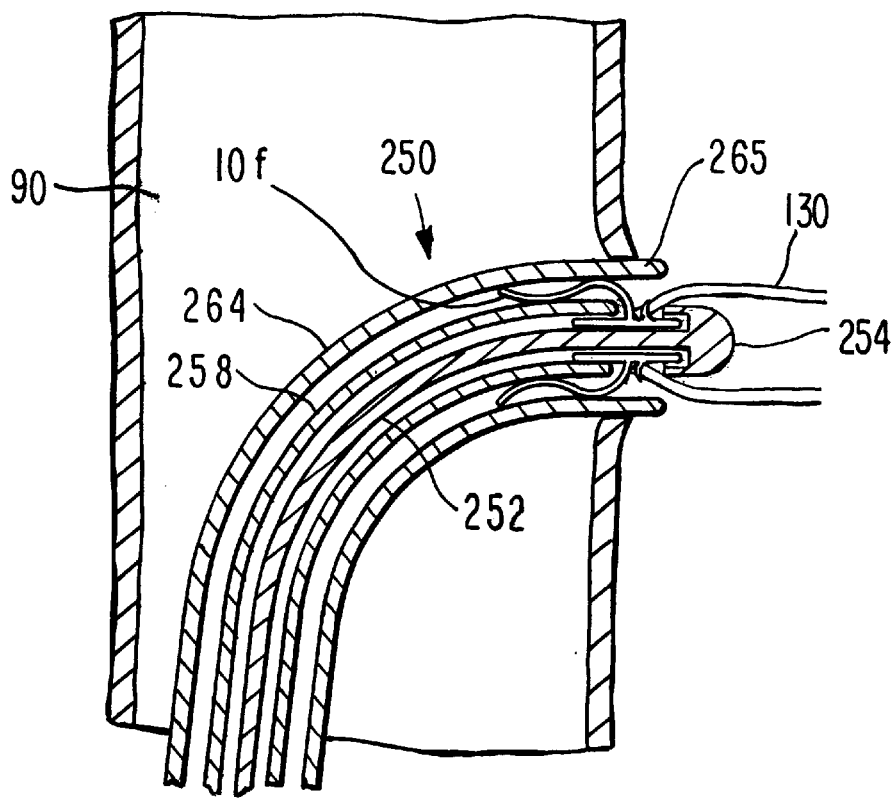
FIG. 25 is a simplified schematic sectional view, illustrating a stage in the installation of the component of FIGS. 20(a)–20(b).

Apparatus 250 is particularly suitable for percutaneous installation of connector 10f. FIG. 25 illustrates apparatus 250 with connector 10f and graft conduit 130 in position within the lumen of existing body conduit 90. Apparatus 250 may be adapted for insertion within and passage along a catheter or other tube. Consequently, the constituent components are preferably flexible. As illustrated in the FIG., a catheter, or sheath 264, may be positioned partially within body conduit 90. The distal end 265 of catheter 264 extends outwardly through an aperture in the wall of conduit 90 and serves as an access port from the inside of conduit 90 to the outside surrounding operative region. (Exemplary catheters useful in connection with the above are described in Goldsteen et al. U.S. Pat. No. 5,976,178, incorporated by reference above, and published PCT patent application WO 99/38441 and Berg et al. U.S. Pat. No. 6,013,190, both incorporated by reference in their entirety herein.) Connector 10f is positioned at the distal end portion of apparatus 250. The various fingers are retained in a configuration substantially parallel with longitudinal axis of apparatus 250. Graft conduit 130 is connected to connector 10f as will be described below. Apparatus 250, along with connector 10f and graft conduit 130, are passed into and along the lumen of body conduit 90 from an access point which may be remote from the anastomosis site.

Figure 26:
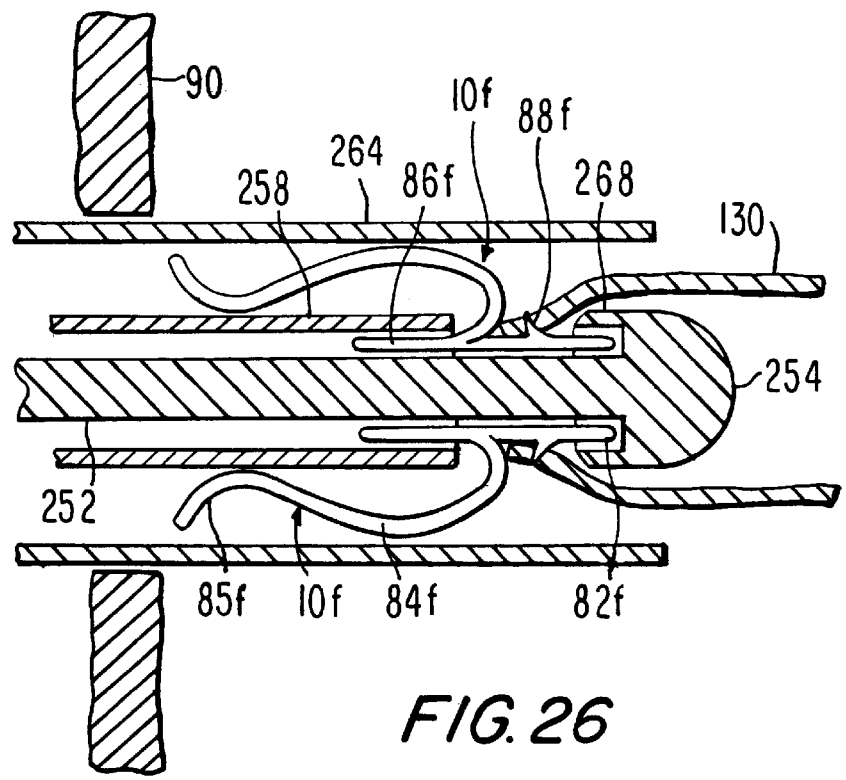
FIG. 26 is an enlarged sectional view, similar to FIG. 25.

As illustrated in FIG. 26, connector 10f is mounted in apparatus 250. (It is noted here that connector 10f is oriented in the opposite direction in FIGS. 25–31, compared with FIGS. 20(a)–20(b), above. For consistency, the distalmost portion is represented in the same direction in these FIGS. During surgical procedures which are typically conducted from outside to inside the body conduit, fingers 86f are the distalmost portions of connector 10f (FIGS. 20(a)–20(b)), i.e., they are furthest from the physician. However, during percutaneous procedures which may be conducted from inside to outside the body conduit, fingers 82f are distalmost. Inner rod or inner sheath 252 may have an outer diameter smaller than the nominal diameter of connector 10f. Connector 10f is fitted around inner rod or inner sheath 252 and radially compressed. Fingers 82f are fitted underneath circumferential flange 268 of distal tip portion 254 and deflected towards parallelism with the longitudinal axis to a flattened distally-extending configuration. Likewise, internal opposition fingers 86f are flattened to a proximally-extending configuration also towards parallelism with the longitudinal axis. Internal opposition fingers 86f are retained in this configuration by outer sleeve 258. Engagement members 88f extend radially outward and engage the graft conduit 130 which is positioned at the distal end portion of inner rod 252 and distal tip 254. Engagement members 88f may alternatively be similar to engagement members 88e (See, FIGS. 19(a)–19(c)), and have a narrow neck portion disposed between a pair of shoulder portions to improve securement of the graft conduit. Catheter 264 is positioned over connector 10f and graft conduit 130, such that the external opposition fingers 84f are deflected to a proximally facing configuration toward parallelism with the longitudinal axis and maintained in this configuration by sheath 264. The configuration illustrated in FIG. 26 is advantageous for passage into and along a body conduit at the operative site. The retraction of the external opposition fingers 84f and 85f within catheter 264 and the atraumatic distal tip 254 minimizes the possibility of injuring adjacent tissue. Apparatus 250 is advanced along body conduit 90 until connector 10f is positioned just outside the body conduit 90 as shown, with radiused finger portions 85f outside the wall of conduit 90.

Figure 27:
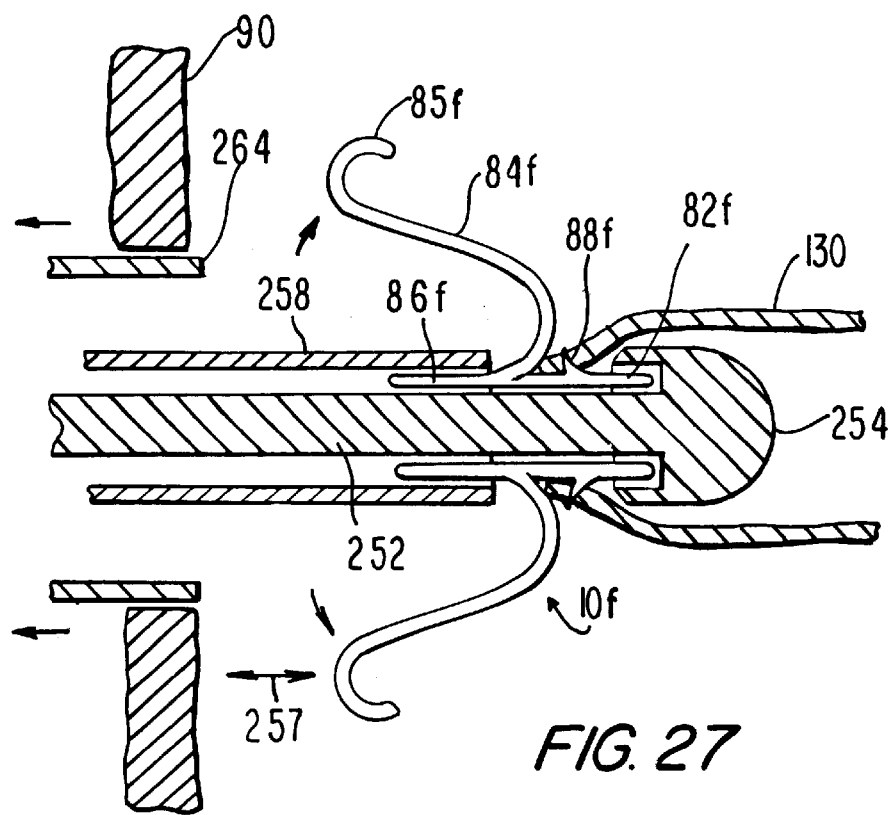
FIG. 27 is an enlarged sectional view, similar to FIG. 26, illustrating a later stage in the installation of the component of FIGS. 20(a)–20(b).

As illustrated in FIG. 27, catheter 264 is withdrawn proximally into conduit 90 until it clears the radiused end portions 85f of external opposition fingers 84f. Connector 10f has been formed such that external opposition fingers 84f are normally biased to a first angle as illustrated in FIG. 27, which is approximately 20°–30° from the longitudinal axis.

Thus, when the catheter 264 is withdrawn proximally, the fingers 84f resiliently move to the first angle shown. At the time the external opposition fingers 84f are deployed, the radiused end portions 85f may be initially a small distance 257 from the outer surface of body conduit 90, due to the pivoting motion of fingers 84f.

Figure 28:
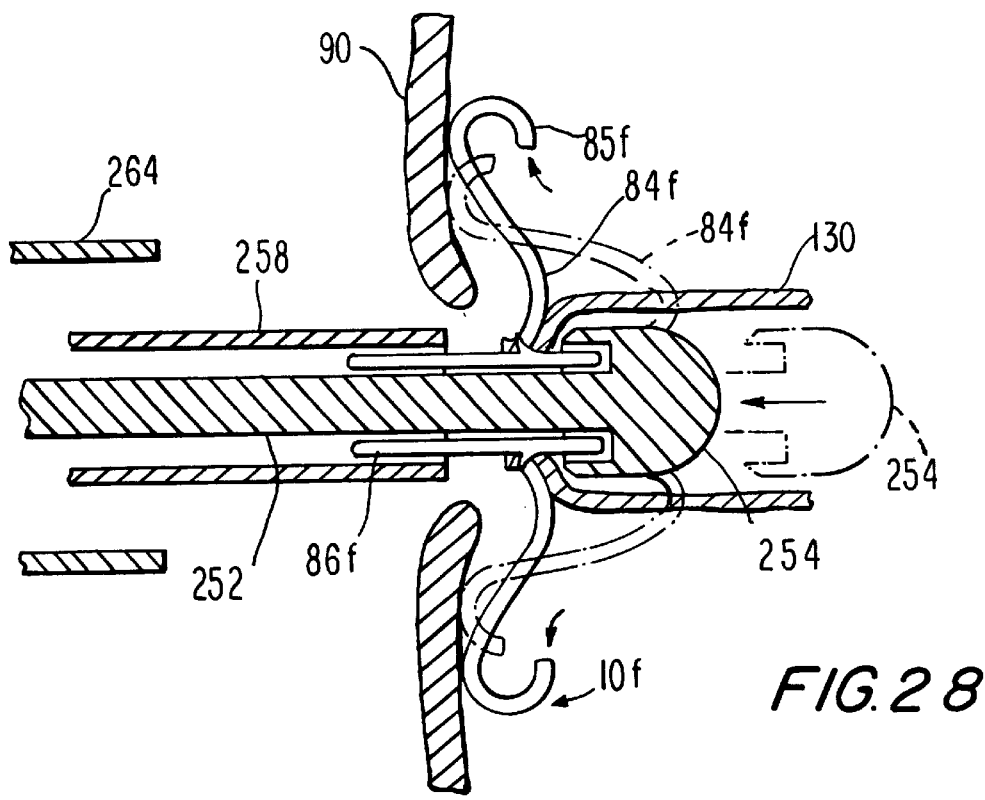
FIG. 28 is an enlarged sectional view, similar to FIG. 27, illustrating yet a later stage in the installation of the component of FIGS. 20(a)–20(b).

The apparatus 250, along with connector 10f is retracted proximally into conduit 90 until the radiused portions 85f contact the outer surface of conduit 90, as illustrated in the dotted line configuration of FIG. 28. Further proximal movement of apparatus 250 results in contact of radiused portions 85f against the outer wall of conduit 90. The shape of radiused portion 85f acts as a camming surface, such that axial movement of connector 10f with respect to conduit 90 causes radiused portion 85f to atraumatically ride over the outer wall of conduit 90 and thereby cam external opposition fingers 84f to a second angle illustrated in solid line.

Figure 29:
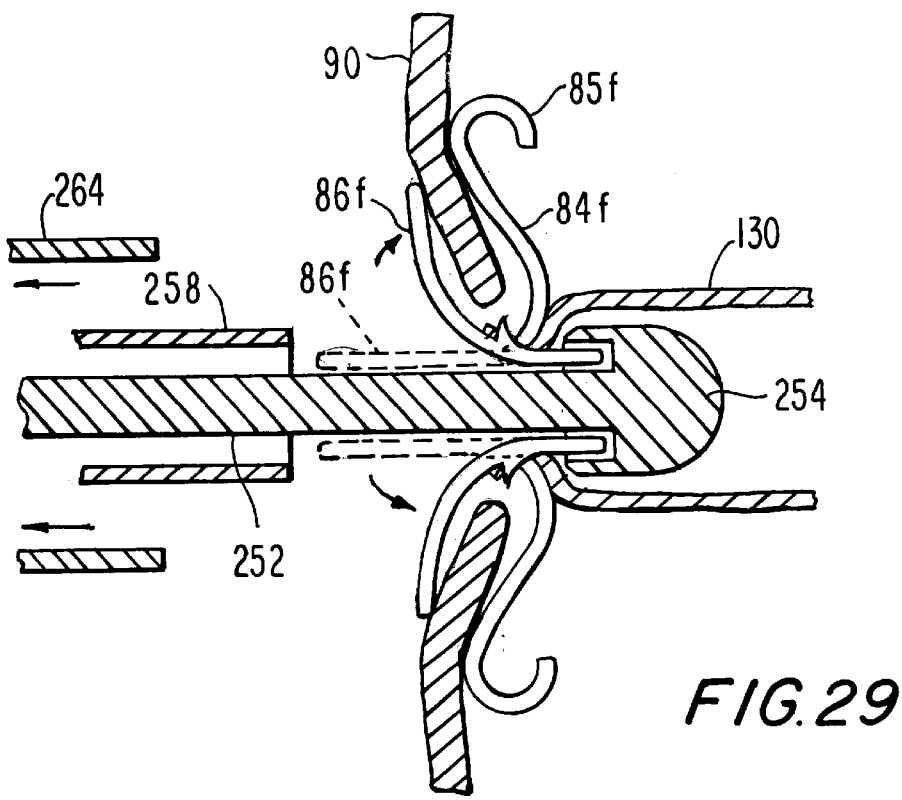
FIG. 29 is an enlarged sectional view, similar to FIG. 28, illustrating a further later stage in the installation of the component of FIGS. 20(a)–20(b).

Outer sleeve 258 is retracted proximally until it clears the internal opposition fingers 86f of connector 10f, as illustrated in FIG. 29. Internal opposition fingers 86f expand outwardly from the slightly flattened configuration (illustrated in dashed line) to a curved, radial configuration in order to engage the inner surface of conduit wall 90. Preferably, retraction of outer sleeve 258 is performed while tension is applied on inner rod or sheath 252 in order to maintain connector 10f and external opposition fingers 84f in an upright, secure position with respect to the wall of conduit 90.

Figure 30:
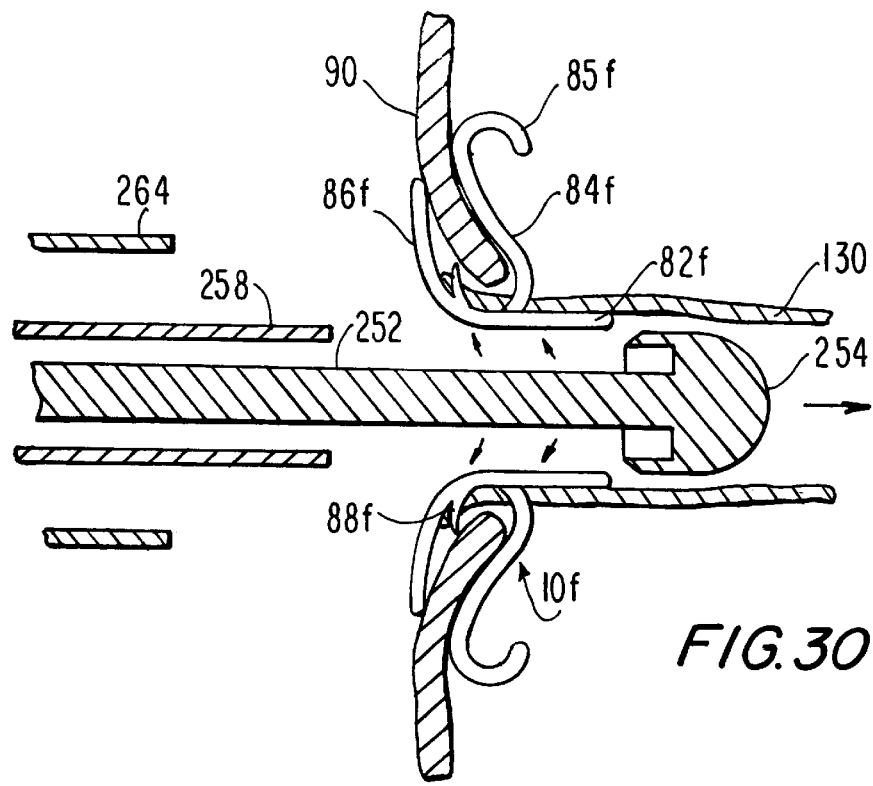
FIG. 30 is an enlarged sectional view, similar to FIG. 29, illustrating another later stage in the installation of the component of FIGS. 20(a)–20(b).
Figure 31:
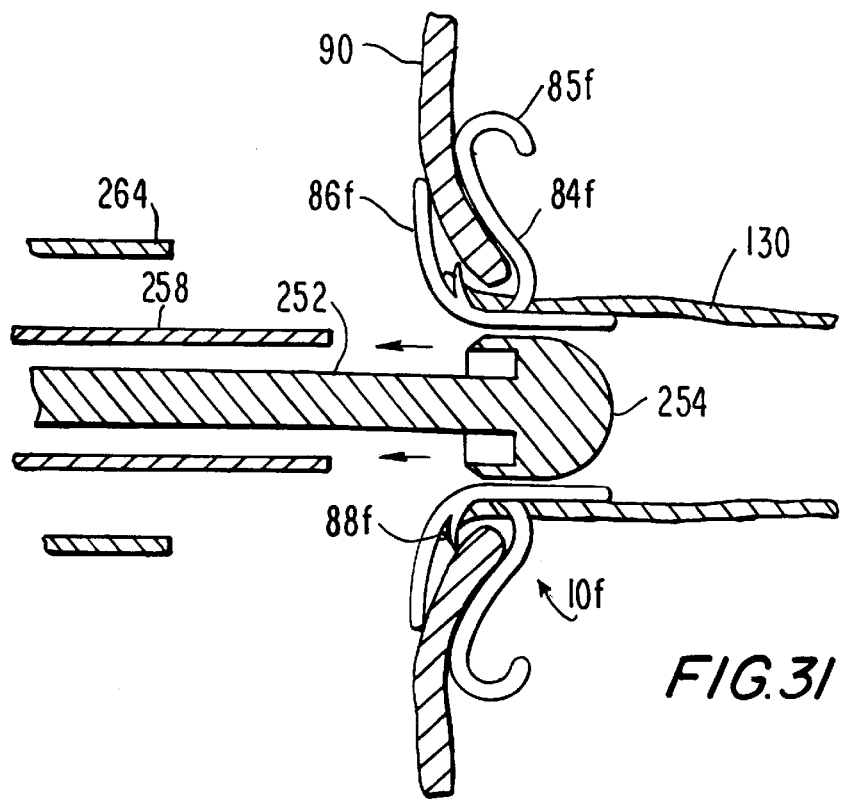
FIG. 31 is an enlarged sectional view, similar to FIG. 30, illustrating withdrawal of the FIG. 24 apparatus from the operative site.

Inner rod 252 is advanced distally such that circumferential flange 268 clears the end portions of radial expansion members 82f (FIG. 30). As the distal tip portion 254 moves distally beyond radial expansion members 82f, the members expand or flare radially outwardly from the flattened configuration (as indicated by the arrows) and thereby partially expand the end portion of graft conduit 130. Such expansion of members 82f improves fluid flow between body conduit 90 and graft conduit 130. Simultaneously, connector 10f expands in diameter in order to provide a secure fluid seal between the conduit 90 and graft conduit 130. Inner rod 252 and outer sleeve 258 may be removed from the anastomosis site. As illustrated in FIG. 31, the connector 10f expands sufficiently that distal tip 254 may pass inside connector and be withdrawn proximally.

Figure 32:
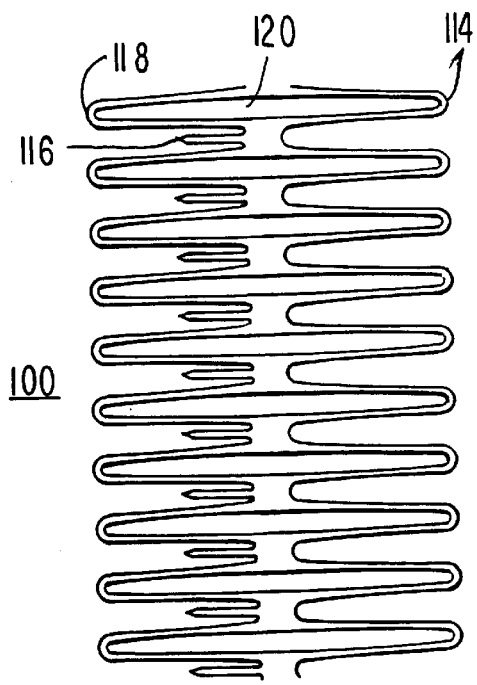
FIG. 32 is a planar representation similar to FIG. 17(a), illustrating another embodiment of the component of FIGS. 1–3.
Figure 33:
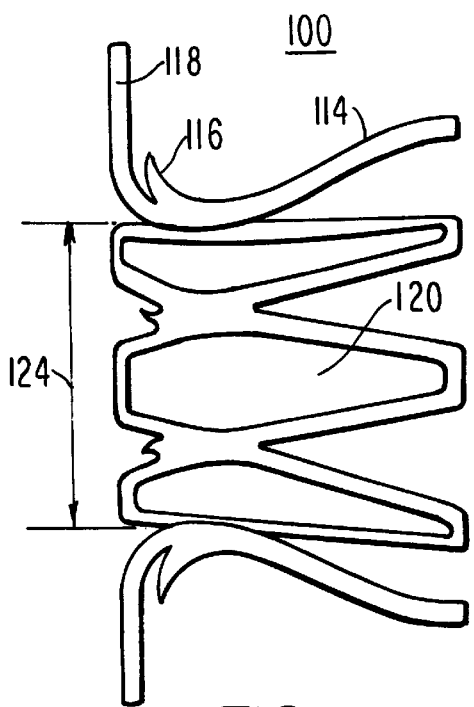
FIG. 33 is a side view in partial cross-section similar to FIG. 14, illustrating the component of FIG. 32 after processing.

An alternative embodiment of a percutaneously deployed connector is connector 100, which is formed from a tube of material substantially as described above with respect to FIG. 2. As illustrated in FIGS. 32–33, component 100 is provided with a plurality of internal support struts 114 and internal opposition fingers 118. Outer opposing fingers are omitted in this particular embodiment, although it is contemplated that such fingers may be useful in accordance with this invention. Radial expansion members 114 are formed with a flared configuration extending axially and radially outward for engaging the interior of the graft conduit, as will be described below. Internal opposition fingers 118 are oriented substantially radially outward. As with connector 10, a plurality of engagement members 116 are provided between adjacent fingers to secure the graft conduit. The planar representation of the machined section of FIG. 32 is an exemplary embodiment, and other configurations are contemplated within the scope of this invention. The connector 100 is given a nominal internal diameter 124. The resilient characteristics of the material and the apertures 120 permit the diameter 124 to be compressed and expanded during mounting and installation.

Figure 34:
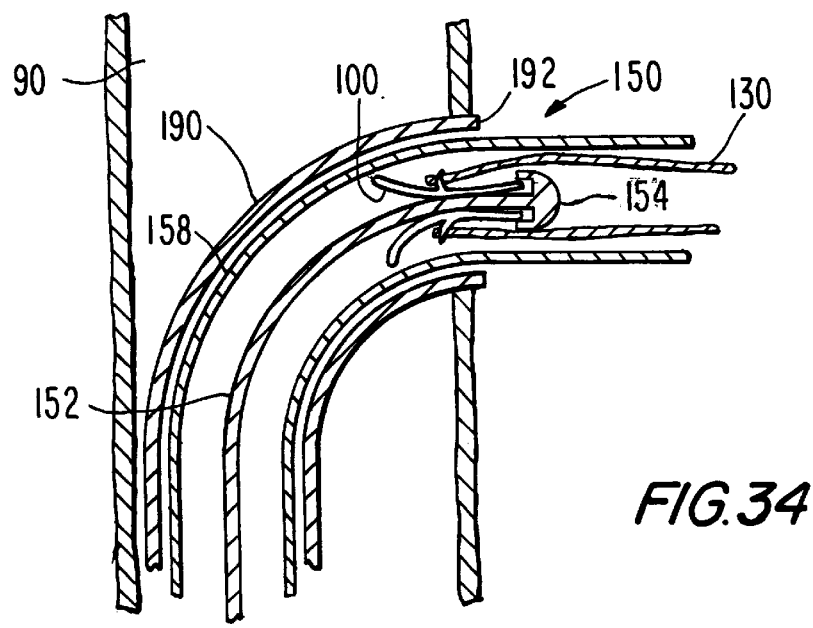
FIG. 34 is a simplified schematic sectional view, illustrating a stage in the installation of the component of FIG. 32.

FIG. 34 illustrates an apparatus 150 particularly suitable for percutaneous installation of connector 100. Similar to apparatus 250 described above (FIG. 24), apparatus 150 may be adapted for insertion within and passage along a catheter or other tube. As illustrated in the FIG., catheter 190 may be positioned partially within body conduit 90, with the distal end 192 of catheter 190 extending outwardly through an aperture in the wall of conduit 90 and serving as an access port from the inside of conduit 90 to the outside surrounding operative region. The distal end of inner rod 152 is provided with a distal tip portion 154, substantially similar to distal tip 254 (FIG. 24). Graft conduit 130 is connected to connector 100 as will be described below. Apparatus 150 retains fingers of component 100 in a substantially parallel configuration.

Figure 35:
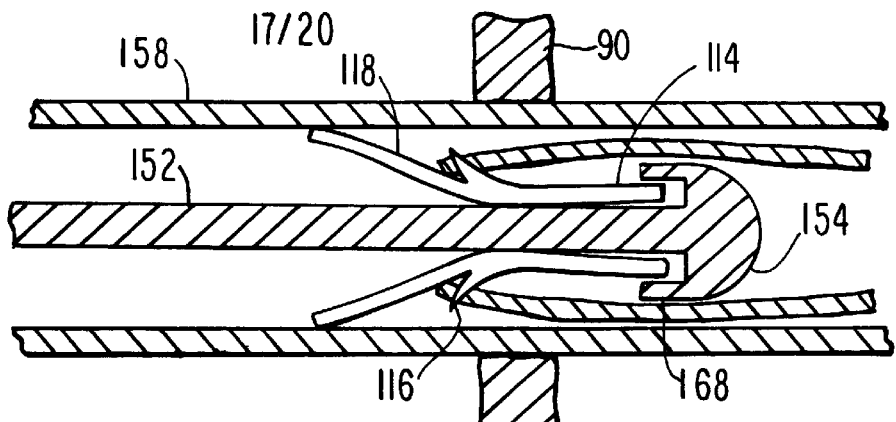
FIG. 35 is an enlarged sectional view, similar to FIG. 34.
Figure 36:
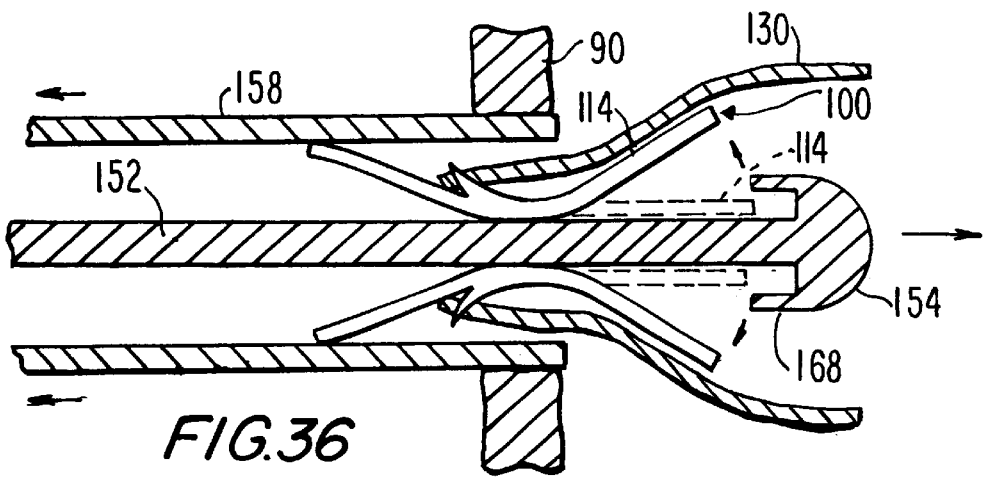
FIG. 36 is an enlarged sectional view, similar to FIG. 35, illustrating a later stage in the installation of the component of FIG. 32.

As illustrated in FIG. 35, inner rod 152 has an outer diameter smaller than the nominal diameter 124 of connector 100 (See, FIG. 33). Connector 100 is fitted around inner rod 152 and compressed. Fingers 114 are fitted underneath circumferential flange 168 of distal tip portion 154 and deflected towards parallelism with the longitudinal axis to a flattened distally-extending configuration. Likewise, internal opposition fingers 118 are slightly flattened to a proximally-extending configuration also toward parallelism with the longitudinal axis. Engagement members 116 extend radially outward and engage the graft conduit 130 which is positioned at the distal end portion of inner rod 152. Engagement members may alternatively be similar to engagement members 88e (See, FIGS. 19(a)–19(c)), and have a narrow neck portion disposed between a pair of shoulder portions to improve securement of the graft conduit. (As FIGS. 34–36 illustrate, it is contemplated that the procedure according to the invention may be conducted through an aperture in conduit 90 without the use of a catheter 190.) Apparatus 150 is advanced along body conduit 90 until connector 100 is positioned at the aperture of body conduit 90 as shown, with radial expansion members 114 extending outside conduit 90 and internal opposition fingers 118 positioned within conduit 90.

Inner rod 152 is advanced distally such that circumferential flange 168 clears the end portions of radial expansion members 114 (FIG. 36). Connector 100 is maintained stationary while outer sleeve 158 is withdrawn proximally. If an introduction catheter 190 is used, such catheter may be withdrawn proximally with outer sleeve 158. As the distal tip portion 154 moves distally beyond radial expansion members 114 and the outer sleeve 158 is withdrawn proximally, the struts expand or flare radially outwardly from the flattened configuration (illustrated in dashed line) and thereby expand the end portion of graft conduit 130. Such expansion of struts 114 minimizes the likelihood of graft conduit 130 moving out of position and back into conduit 90 during and after installation, and improves fluid flow between body conduit 90 and graft conduit 130.

Figure 37:
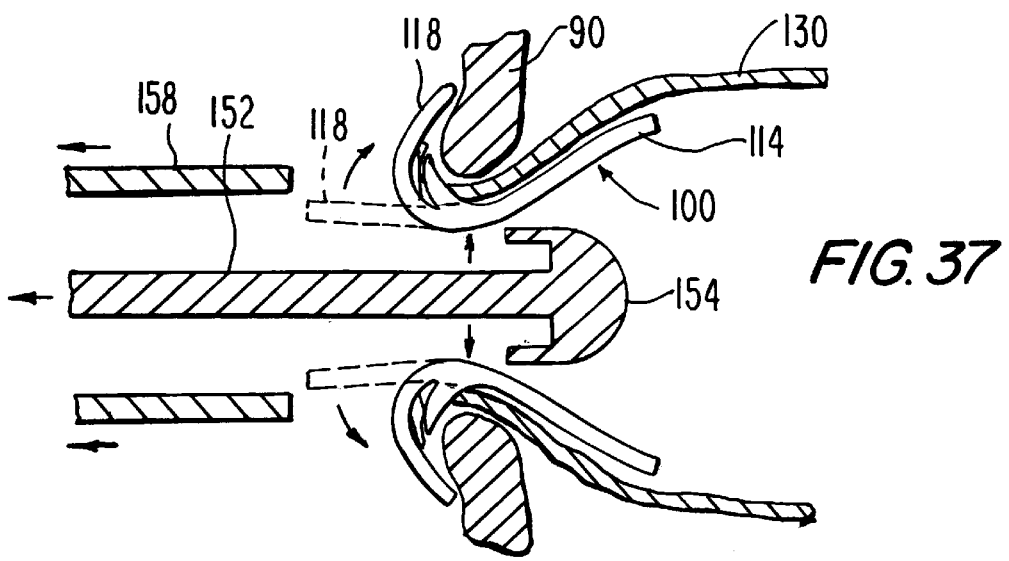
FIG. 37 is an enlarged sectional view, similar to FIG. 36, illustrating yet a later stage in the installation of the component of FIG. 32.

Outer sleeve 158 is further retracted proximally until it clears the internal opposition fingers 118 of connector 100, as illustrated in FIG. 37. Internal opposition fingers 118 expand outwardly from the slightly flattened configuration (illustrated in dashed line) to a curved, radial configuration in order to engage the inner surface of conduit wall 90. Simultaneously, connector 100 expands in diameter in order to provide a secure fluid seal between the conduit 90 and graft conduit 130. Inner rod 152 and outer sleeve 158 may be removed from the anastomosis site. The connector 100 expands sufficiently that distal tip 154 may pass inside connector and be withdrawn proximally.

As with apparatus 150 illustrated in FIGS. 34–37 above, apparatus 250 may be deployed from the lumen of a catheter 290 or other tube which has passed through an aperture in body conduit 90 from internally to the outside of the conduit. (It is also contemplated that apparatus may be deployed from an aperture in a body conduit without the use of a separate catheter.)

Figure 38:
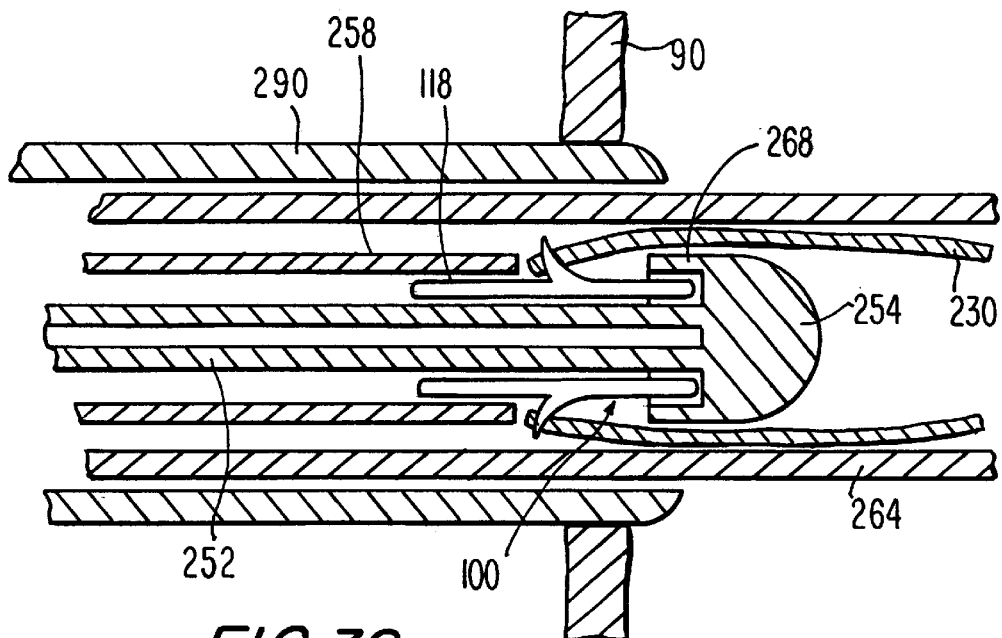
FIG. 38 is a simplified sectional view of the component of FIG. 32 and a graft conduit mounted in the FIG. 24 apparatus, illustrating a stage in the installation of the FIG. 32 component in the patient.

Prior to deploying apparatus 250, connector 100 is mounted in the apparatus (FIG. 38). As shown in FIG. 33, connector 100 has a nominal internal diameter 124 which is larger than the outer diameter of both inner rod 252 and distal tip 254. Connector 100 is passed over distal tip 254, and the resilient characteristics described above permit the connector 100 to be compressed to a smaller diameter around inner rod 252. The struts 114 are compressed from the flared configuration of FIG. 33 toward parallelism with the longitudinal axis to a substantially distal flattened configuration and maintained in such configuration by collar 268. Likewise, the internal opposition fingers 118 are deflected toward parallelism with the longitudinal axis and maintained in a substantially flattened, proximally-extending configuration between inner rod 252 and outer sleeve 258. Engagement members 116, which extend radially outward, engage the graft conduit 230. Sheath 264 coaxially surrounds apparatus 250 and graft conduit 230.

Figure 39:
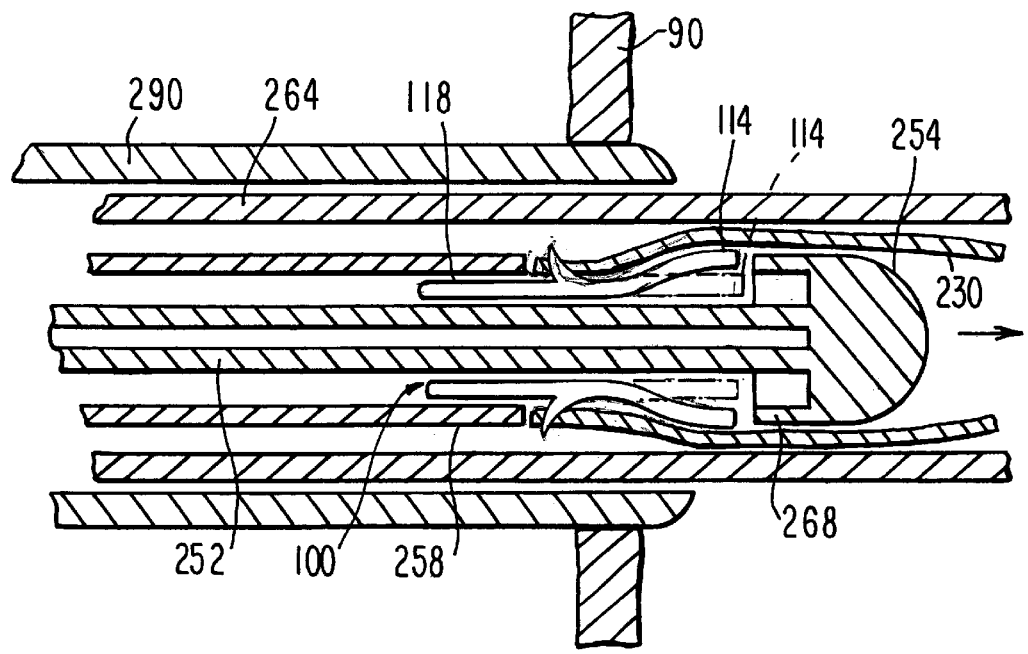
FIG. 39 is a simplified sectional view similar to FIG. 38, illustrating a further stage in the installation.

As illustrated in FIG. 39, apparatus 250 is advanced until radial expansion members 114 are disposed beyond the wall of conduit 90. When the physician has determined that connector 100 is properly positioned, inner rod 252, along with distal tip 254 are moved distally, while outer sleeve 258 remains stationary. When collar 268 is advanced beyond the distalmost end of connector 100, strut 114 is permitted to move from its straightened configuration (illustrated in dashed line) to a radially flared position engaging the inner surface of graft conduit 230. Catheter 290 and sheath 264 are maintained stationary, so that struts 114 and graft conduit 230 are constrained within the lumen of sheath 264.

Figure 40:
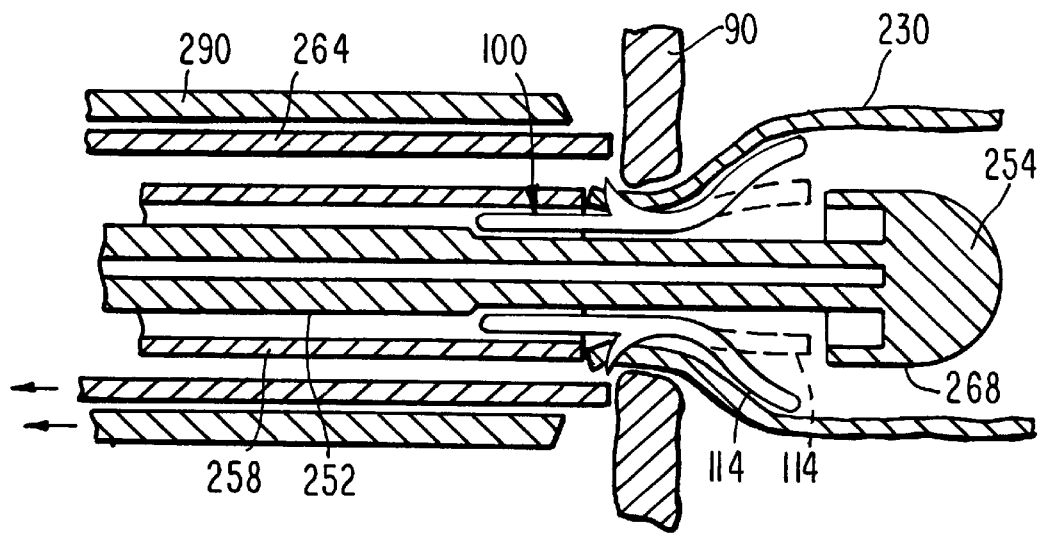
FIG. 40 is a simplified sectional view similar to FIG. 39, illustrating another stage in the installation.

As illustrated in FIG. 40, catheter 290 and sheath 264 are withdrawn proximally into conduit 90, permitting the side walls of conduit 90 to close around graft 230, which is exposed from sheath 264. Struts 114 are permitted to move from the slightly deflected configuration of FIG. 39 (illustrated in dashed line) to a radially flared position engaging the inner surface of graft conduit 230. Graft conduit 230 is expanded in overall diameter, which assists in preventing graft conduit 230 from moving proximally back into conduit 90.

Figure 41:
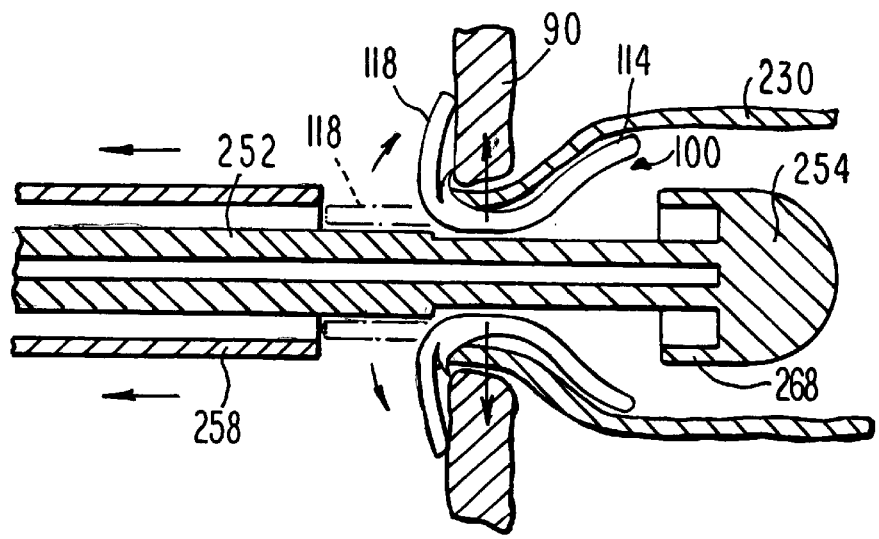
FIG. 41 is a simplified sectional view similar to FIG. 40, illustrating yet another stage in the installation.

Outer sleeve 258 is subsequently withdrawn proximally with respect to inner rod 252 (FIG. 41). When outer sleeve 258 is moved beyond the proximal end of connector 100, internal opposition fingers 118 move from the flattened configuration (illustrated in dashed line) to the curved configuration to engage the inner surface of the conduit wall. Simultaneously, the diameter of connector 100 expands to a larger diameter as indicated by the arrows. This provides a seal between the graft 230 and conduit 90. In addition, the increased internal diameter permits the distal tip 254 to be withdrawn proximally through connector 100 (not shown). Once the connector 100 has been properly positioned, inner rod 252 and outer sleeve 258 are withdrawn from the conduit 90.

FIGS. 42–46 illustrate a further embodiment of the subject invention. Tool 500 is provided to facilitate the mounting of a connector onto an end portion of the graft conduit 30. Tool 500 is sized and configured to provide a flared, or everted edge to the graft conduit. This flared configuration of the graft assists in the connection with the tubular body structure by facilitating blood flow from the graft conduit to the body conduit. Furthermore, this configuration helps to seal the opening in the body conduit into which the graft is inserted and accommodates size variations between the graft and the opening. If the graft conduit is a natural blood vessel, e.g., the saphenous vein, this configuration permits the blood to remain in contact with endothelium tissue during the transition between the graft and the body conduit.

As illustrated in FIGS. 42–43, eversion tool 500 has a tubular body portion 502 sized and configured for insertion into the graft conduit in the axial direction 506, and a larger flange portion 508 which remains outside the graft conduit. A plurality of apertures 512 are defined in flange portion 508, and extend axially within flange portion 508. (See, FIG. 43.)

Eversion tool 500 is inserted into the end portion of graft conduit 30 (FIG. 42). Tubular portion 502 is advanced within the graft conduit until the end of graft conduit abuts flange portion 508, which has a surface disposed at approximately a right angle with respect to tubular portion 502. Further axial advancement of tool 500 with respect to graft conduit will cause the end portion of the graft to flare outwardly against the flange portion to create flange 530. As shown in the FIG., advancement of tool 500 results in the eversion of graft conduit.

FIG. 44 illustrates the installation of a connector 550 to the graft conduit 30. Connector 550 may assume a number of different configurations. In a preferred embodiment, connector 550 includes a medial band portion 552. A plurality of fingers 554 and 556 are provided on both axial end portions of the band portion 552. Preferably, fingers 554 and 556 are fabricated of a resilient material and assume a radially outward or "U"-shaped configuration when viewed from a plane extending radially out from the tubular portion in the relaxed or unstressed configuration (see, FIG. 45). Fingers 554 and 556 assume a flattened axial configuration substantially parallel with axis 506 when in the stressed configuration.

As illustrated in FIG. 44, the connector 550 is positioned coaxially surrounding the graft conduit 30. A deployment sheath 560 is positioned in a coaxially surrounding configuration around connector 550 and graft conduit 30. This placement of the sheath 560 deflects fingers 554 and 556 toward parallelism with axis 506, such that internal opposition fingers 554 are deflected distally and external opposition fingers 556 are deflected proximally. Once this flattened configuration has been achieved, connector 550 is advanced distally toward flange 508. The internal opposition fingers 554 are advanced to pierce the flange 530 of the graft conduit 30 and pass into the apertures 512 defined in the flange 508.

As illustrated in FIG. 45, deployment sheath 560 and eversion tool 500 are removed from the graft conduit 30. Internal 554 and external opposition fingers 556 of connector 550 return to their unstressed configuration. Internal opposition fingers 554, which have pierced the flange 530 of graft conduit 30, return to the radially outward configuration and therefore maintain the flange 530 in an everted configuration.

Installation of the graft conduit 30 into a body conduit 90 having connector 550 attached is performed substantially as described above with respect to FIGS. 34–37. Connector 550 and graft conduit 30 may be mounted within an outer sheath, such as sheath 58 of FIGS. 8–13. Internal 554 and external opposition fingers 556 are maintained in a flattened configuration similar to that shown in FIG. 44. When connector is positioned in the body conduit 90, the sheath 58 is withdrawn, and fingers return to their unstressed configuration as illustrated in FIG. 46.

It will be understood that the foregoing is only illustrative of the principles of the invention, and that still other modifications can be made by those skilled in the art without departing from the scope and spirit of the invention. For example, the various materials and dimensions mentioned herein are only examples, and other materials and dimensions can be used if desired.

What is claimed is:

1. Apparatus for connecting an axial end portion of a tubular graft conduit to a side wall of a patient's tubular body conduit via an aperture in that side wall comprising:

connector having a plurality of fingers extending from an axial end of the connector, the fingers being movable between a first configuration wherein the fingers extend radially from the connector to a second configuration wherein the fingers extend substantially axially from the connector;

mandrel sized for insertion into the end of the graft conduit to radially expand the end portion of the graft conduit, the mandrel defining a plurality of openings for receiving the fingers in the second configuration; and a sleeve configured to surround the connector and the tubular graft conduit and to deflect the fingers toward the second configuration to pierce the radially expanded portion of the graft conduit and be received in the openings.

2. Apparatus defined in claim 1, wherein the fingers are configured to resiliently return to the first configuration.

3. Method of connecting an axial end portion of a tubular graft conduit to a side wall of a patient's tubular body conduit via an aperture in that side wall comprising:

providing a connector having a plurality of fingers, the fingers being movable between a first configuration wherein the fingers extend radially outward to a second configuration wherein the fingers extend substantially axially;

expanding an axial end portion of the graft conduit to a radially flared configuration;

piercing the flared end portion of the graft conduit with the fingers from an outer surface of the graft to an inner surface of the graft while maintaining the fingers in the second configuration; and allowing the fingers to return to the first configuration such that the end portion of the graft conduit is maintained in the radially flared configuration.

4. The method defined in claim 3, further comprising:

providing a mandrel sized for insertion into the axial end of the graft conduit to radially flare the end portion of the graft conduit, wherein expanding the end portion of the graft comprises inserting the mandrel into the end of the graft conduit such that the end portion of the graft conduit expands to the flared configuration.

* * * * *